(12) United States Patent
Henry et al.

(10) Patent No.: US 8,363,215 B2
(45) Date of Patent: Jan. 29, 2013

(54) METHODS FOR EMPLOYING STROBOSCOPIC SIGNAL AMPLIFICATION AND SURFACE ENHANCED RAMAN SPECTROSCOPY FOR ENHANCED TRACE CHEMICAL DETECTION

(75) Inventors: Kent D. Henry, Laramie, WY (US); Blase Yamona, Lakewood, CO (US); John S. Lovell, Golden, CO (US)

(73) Assignee: ADA Technologies, Inc., Littleton, CO (US)

( * ) Notice: Subject to any disclaimer, the term of this patent is extended or adjusted under 35 U.S.C. 154(b) by 1373 days.

(21) Appl. No.: 12/020,419

(22) Filed: Jan. 25, 2008

(65) Prior Publication Data
US 2012/0133932 A1 May 31, 2012

Related U.S. Application Data

(60) Provisional application No. 60/886,583, filed on Jan. 25, 2007.

(51) Int. Cl.
*G01J 3/44* (2006.01)
*G01J 3/28* (2006.01)
*G01J 3/00* (2006.01)
*B82Y 20/00* (2011.01)

(52) U.S. Cl. ......... 356/301; 356/300; 356/326; 977/957
(58) Field of Classification Search .................. 356/445, 356/417, 246, 301, 317, 300, 326; 436/155, 436/171, 59, 165, 164, 94; 422/78, 68.1; 250/494.1, 390.04
See application file for complete search history.

(56) References Cited

U.S. PATENT DOCUMENTS

| | | | |
|---|---|---|---|
| 3,463,591 A | 8/1969 | Franken et al. |
| 3,680,959 A | 8/1972 | Schuch et al. |
| 3,748,905 A | 7/1973 | Fletcher et al. |
| 3,853,503 A | 12/1974 | Folmer, Jr. |
| 4,040,411 A | 8/1977 | Rust |
| 4,580,440 A | 4/1986 | Reid et al. |
| 4,718,268 A | 1/1988 | Reid et al. |
| 4,754,655 A | 7/1988 | Parker et al. |
| 4,819,477 A | 4/1989 | Fisher et al. |
| 4,820,920 A | 4/1989 | Bather |
| 4,867,796 A | 9/1989 | Asmus et al. |
| 4,982,176 A | 1/1991 | Schwarz |
| 5,017,780 A | 5/1991 | Kutscher et al. |
| 5,092,155 A | 3/1992 | Rounbehler et al. |
| 5,092,157 A | 3/1992 | Achter et al. |
| 5,092,218 A | 3/1992 | Fine et al. |
| 5,092,220 A | 3/1992 | Rounbehler |
| 5,112,127 A | 5/1992 | Carrabba et al. |

(Continued)

FOREIGN PATENT DOCUMENTS

| | | |
|---|---|---|
| EP | 0485425 | 5/1992 |
| WO | WO 94/27145 | 11/1994 |

(Continued)

OTHER PUBLICATIONS

"Global Security Solutions" available at http://www.global-security-solutions.com/, printed Sep. 11, 2009.

(Continued)

*Primary Examiner* — Sang Nguyen
(74) *Attorney, Agent, or Firm* — Sheridan Ross PC

(57) ABSTRACT

In one embodiment, a method and system is provided for detecting target materials using a combination of stroboscopic signal amplification and Raman spectroscopy techniques.

21 Claims, 31 Drawing Sheets

U.S. PATENT DOCUMENTS

| | | | |
|---|---|---|---|
| 5,122,127 A | 6/1992 | Stanley | |
| 5,138,889 A | 8/1992 | Conrad | |
| 5,147,611 A | 9/1992 | Stout et al. | |
| 5,149,972 A | 9/1992 | Fay et al. | |
| 5,278,418 A | 1/1994 | Broadhurst | |
| 5,476,794 A | 12/1995 | O'Brien et al. | |
| 5,580,733 A | 12/1996 | Levis et al. | |
| 5,585,575 A | 12/1996 | Corrigan et al. | |
| 5,600,700 A | 2/1997 | Krug et al. | |
| 5,663,561 A | 9/1997 | Franzen et al. | |
| 5,693,152 A | 12/1997 | Carron | |
| 5,751,897 A | 5/1998 | Van Alstyne | |
| 5,782,253 A | 7/1998 | Cates et al. | |
| 5,842,995 A | 12/1998 | Mahadevan-Jansen et al. | |
| 5,859,375 A | 1/1999 | Danylewych-May et al. | |
| 5,862,273 A | 1/1999 | Pelletier | |
| 5,870,886 A | 2/1999 | Norton | |
| 5,904,900 A | 5/1999 | Bleuse et al. | |
| 5,942,699 A | 8/1999 | Ornath et al. | |
| 5,955,729 A | 9/1999 | Nelson et al. | |
| 5,965,884 A | 10/1999 | Laiko et al. | |
| 5,972,638 A | 10/1999 | Burlage et al. | |
| 6,018,389 A | 1/2000 | Kyle et al. | |
| 6,085,601 A | 7/2000 | Linker et al. | |
| 6,127,935 A | 10/2000 | Davidson et al. | |
| 6,191,406 B1 | 2/2001 | Nelson et al. | |
| 6,353,476 B1 | 3/2002 | Allen et al. | |
| 6,446,514 B1 | 9/2002 | Danylewych-May et al. | |
| 6,477,907 B1 | 11/2002 | Chambers et al. | |
| 6,558,626 B1 | 5/2003 | Aker et al. | |
| 6,558,956 B1 | 5/2003 | Carron et al. | |
| 6,614,523 B1 | 9/2003 | Boss et al. | |
| 6,621,574 B1 | 9/2003 | Forney et al. | |
| 6,692,694 B1 | 2/2004 | Curry et al. | |
| 6,723,564 B2 | 4/2004 | Hillenkamp | |
| 6,730,923 B1 | 5/2004 | May et al. | |
| 6,734,423 B2 | 5/2004 | Bryden | |
| 6,735,368 B2 | 5/2004 | Parker et al. | |
| 6,753,396 B2 | 6/2004 | Ulbricht et al. | |
| 6,775,448 B2 | 8/2004 | Zoorob | |
| 6,788,863 B2 | 9/2004 | Parker et al. | |
| 6,797,242 B2 | 9/2004 | Neumann et al. | |
| 6,797,944 B2 | 9/2004 | Nguyen et al. | |
| 6,828,795 B2 | 12/2004 | Krasnobaev et al. | |
| 6,838,663 B2 | 1/2005 | Coon et al. | |
| 6,856,737 B1 | 2/2005 | Parker et al. | |
| 6,861,646 B2 | 3/2005 | Motchkine et al. | |
| 6,870,155 B2 | 3/2005 | Krasnobaev et al. | |
| 6,888,128 B2 | 5/2005 | Krasnobaev et al. | |
| 6,895,804 B2 | 5/2005 | Lovell et al. | |
| 6,897,951 B2 | 5/2005 | Womble et al. | |
| 6,909,542 B2 * | 6/2005 | Sasaki | 359/385 |
| 6,947,132 B1 | 9/2005 | Boss et al. | |
| 6,959,127 B2 | 10/2005 | Zoorob | |
| 6,967,717 B1 | 11/2005 | Boss et al. | |
| 7,016,586 B2 | 3/2006 | Zoorob et al. | |
| 7,027,701 B2 | 4/2006 | Parker et al. | |
| 7,084,397 B2 | 8/2006 | Hirano et al. | |
| 7,098,672 B2 | 8/2006 | Belyakov et al. | |
| 7,116,878 B2 | 10/2006 | Zoorob et al. | |
| 7,140,265 B2 | 11/2006 | McGrill et al. | |
| 7,162,132 B2 | 1/2007 | Parker et al. | |
| 7,244,288 B2 | 7/2007 | Belyakov et al. | |
| 7,248,770 B2 | 7/2007 | Parker et al. | |
| 7,574,930 B2 | 8/2009 | Bunker | |
| 7,576,320 B2 | 8/2009 | Bunker et al. | |
| 7,688,440 B2 * | 3/2010 | Clarke et al. | 356/301 |
| 7,833,802 B2 * | 11/2010 | Henry et al. | 436/155 |
| 2003/0039299 A1 | 2/2003 | Horovitz et al. | |
| 2003/0133105 A1 | 7/2003 | Gorelik et al. | |
| 2003/0155504 A1 | 8/2003 | Motchkine et al. | |
| 2004/0142484 A1 * | 7/2004 | Berlin et al. | 436/171 |
| 2005/0047702 A1 | 3/2005 | Parker et al. | |
| 2005/0079626 A1 | 4/2005 | Kunz | |
| 2005/0235739 A1 | 10/2005 | Lovell et al. | |
| 2005/0248758 A1 | 11/2005 | Carron et al. | |
| 2006/0062540 A1 | 3/2006 | Zoorob et al. | |
| 2006/0119853 A1 | 6/2006 | Baumberg et al. | |
| 2006/0219937 A1 | 10/2006 | Henry et al. | |
| 2006/0228251 A1 | 10/2006 | Schneberger et al. | |
| 2006/0256340 A1 | 11/2006 | Hansen et al. | |
| 2007/0015288 A1 | 1/2007 | Hulteen et al. | |
| 2007/0056388 A1 | 3/2007 | Henry et al. | |
| 2007/0215725 A1 | 9/2007 | Bunker | |
| 2008/0290810 A1 | 11/2008 | Kiernan et al. | |

FOREIGN PATENT DOCUMENTS

| | | |
|---|---|---|
| WO | WO 99/01750 | 1/1999 |

OTHER PUBLICATIONS

Handschh, Martin, et al., Laser-induced molecular desorption and particle ejection fromorganic films, 1999, Applied Surface Science, vol. 137, pp. 125-135.

Kawai et al. "Application Note #18: Raman Spectroscopy for Homeland Defense Applications" by InPhotonics, 2004, pp. 1-4.

Thiesan et al., "Survey of Commercially Available Explosives Detection Technologies and Equipment 2004", Sandia National Laboratories, Document No. 208861, Feb. 2005, 97 pages.

International Preliminary Report on Patentability for International (PCT) Patent Application No. PCT/US08/52114, mailed Aug. 6, 2009.

"2,4-Dinitrotoluene Material Safety Data Sheet", Sep. 1997, Toxic Air Contaminant Identification Seriers, pp. 437-439.

Fryer et al., "Dependence of the Glass Transition Temperature of Polymer Films on Interfacial Energy and Thickness", 2001, Macromolecules, vol. 37, No. 16, pp. 5627-5634.

K. Fransson; "The Trigger System of the CELSIUS/WASA Detector," Physica Scripta T99,(2002), pp. 176-182.

Lewis, J., "Recommendation to List 2,4,6-Trinitrotoluene (TNT) as a Potential Pollutant", Apr. 2001, pp. 1-8.

M. Mayer et al.; "Performance of CdZnTe Strip Detectors as Submillimeter Resolution Imaging Gamma Radiation Spectrometers," undated, 5 pages.

Paul Tompkins et al.; "Icebreaker: An Exploration of the Lunar South Pole," copyright 1999 by the Space Studies Institute, 11 pages.

V. Dabur et al.; "Position-sensitive detector for the 6-meter optical telescope," printed Nov. 13, 2003, 6 pages, available at http://andv.org/pdf/astro-ph/0310353.

V.A. Morosov et al.; "2.pi. spectrometer: A new apparatus for the investigation of ion surface interaction," Rev. Sci. Instrum. 67(6) (Jun. 1996), pp. 2163-2170.

Yvan Simard et al.; "New technology for the detection of micronekton: multivariate acoustics, sampling and data analysis strategies," printed Nov. 13, 2003, 24 pages, available at http://pulson.seos.uvic.ca/meeting/scor2000/simard/simard.html.

Prism (optics), Wikipedia, the free encyclopedia, available at http://en.wikipedia.org/wiki/Prism_%28optics%29, printed Jan. 18, 2008, pp. 4.

Optical instruments—Wikipedia, the free encyclopedia, available at http://en.wikipedia.org/wiki/Optical_instrument, printed Jan. 18, 2008, pp. 2.

Lens (optics)—Wikipedia, the free encyclopedia, available at http://en.wikipedia.org/wiki/Lens_%28optics%29, pp. 15.

Mirror—Wikipedia, the free encyclopedia, available at http://en.wikipedia.org/wiki/Mirror, printed Jan. 18, 2008, pp. 11.

Internet web page for Mesophotonics regarding Klarite, available at http://www.mesophotonics.com/products/klarite.html, cite updated May 4, 2007, pp. 1-2.

Kambhampati, et al., "On Chemical Mechanism of Surface Raman Scattering: Experiment and Theory", Chem. Phy. 1998(108): 5013-5026.

International Search Report for International (PCT) Patent Application No. PCT/US08/52114, mailed Jul. 8, 2008.

Written Opinion for International (PCT) Patent Application No. PCT/US08/52114, mailed Jul. 8, 2008.

Background for the above-captioned application (previously provided).

\* cited by examiner

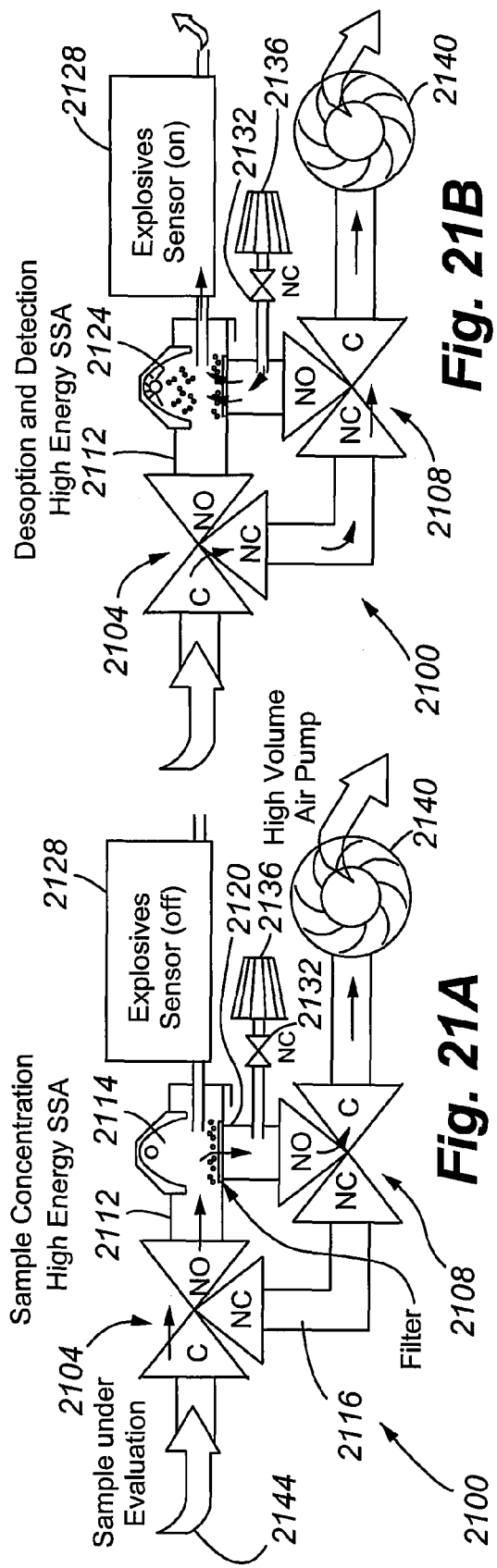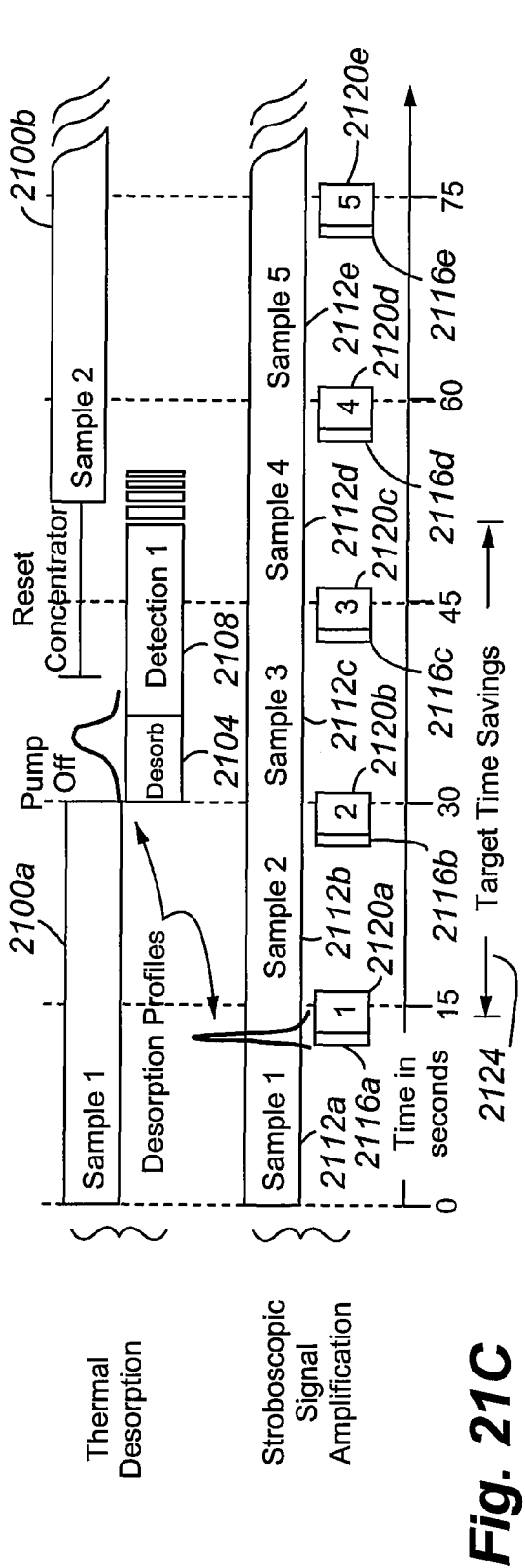
Fig. 21A
Fig. 21B
Fig. 21C

METHODS FOR EMPLOYING STROBOSCOPIC SIGNAL AMPLIFICATION AND SURFACE ENHANCED RAMAN SPECTROSCOPY FOR ENHANCED TRACE CHEMICAL DETECTION

CROSS REFERENCE TO RELATED APPLICATION

The present application claims the benefits of U.S. Provisional Application Ser. No. 60/886,583, filed Jan. 25, 2007, entitled "Methods for Employing SSA and SERS for Enhanced Trace Chemical Detection", which is incorporated herein by this reference in its entirety.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Contract No. W911QX-04-C-0006 awarded by the Department of Defense.

FIELD OF THE INVENTION

The invention relates generally to chemical and microbe detection and particularly to detection of trace chemicals, such as drugs and explosives.

BACKGROUND OF THE INVENTION

Explosives and other controlled substances, such as drugs, have become major societal problems. Increasingly, terrorist acts using explosives are becoming a problem not only for countries in the Middle East but also for Western countries in other parts of the world. Explosives constitute a weapon used by terrorists and insurgents, and may be hidden in a myriad of devices; however, it is typically difficult for a person handling explosives to avoid contamination after coming into contact with an explosive or explosive device because explosives readily adhere to surfaces.

In addition to explosives, drug abuse has been a longstanding problem for Western countries and consumes large amounts of law enforcement resources each year. Canines, metal detectors, and "sniffer" detectors have been used at various locations, such as airports, border crossings, and the like, to detect explosive devices and illegal drugs. These measures have had mixed success.

Another measure that has been employed to detect contraband substances has been to collect loose particles from surfaces or skin with a vacuum cleaner or a swipe. The swipe or the particles collected by the vacuum are then heated to release the vaporizable material for analysis. This approach is in routine use at airports throughout the world for screening airline passengers. An example of such a system is the Barringer™ Ion Scan System™; however, this technique has drawbacks. For example, the use of swipes or particle vacuums is an intermittent process, which requires manual intervention between the sampling and analysis. This is a time consuming approach that is inherently slow.

Previously disclosed devices for volatilizing certain substances for detection include a high-energy apparatus disclosed in U.S. Pat. No. 6,895,804. The content of U.S. Pat. No. 6,895,804 is incorporated herein by reference in its entirety. The landmine detection apparatus of the '804 patent applies a relatively high amount of energy to the sample target that is generally intended to be soil. To provide the requisite energy, the radiation source of the '804 patent is powered by a relatively high amount of energy, and therefore, is limiting in its ability to serve as a self-contained backpack unit, hand-held device, or other relatively compact portable device. In addition, high-energy strobes are slow to recharge, utilize kilowatts of energy to power, and are heavy as a self-contained unit that includes a power source.

U.S. Pat. No. 6,828,795, incorporated herein by reference, suggests use of an ion mobility spectrometer with a heat source, but energy levels have not been provided. U.S. Patent Application Publication No. 2005/0007119 A1, related to the '795 patent, is also incorporated herein by reference. The '795 patent discloses using an electrostatic precipitator to take out particulates, presumably to keep them out of the ion mobility spectrometer.

Typical trace explosive detectors employing vapor and/or particle analyses rely on an interval-based analysis that requires discrete and separate steps for (1) sampling and (2) detection. The combination of these two steps may take anywhere from 15 to 60 seconds, or more. Thus, it would be advantageous to provide an apparatus for sampling multiple target surfaces while the detector is processing the sampled information.

There is a need for a field-portable, enhanced Trace Explosive Detection System (eTEDS) that can provide, relative to existing eTEDS systems, improved signal enhancement, detect target substances in near-real-time, use relatively low levels of power for each measurement, and/or can withstand rough handling during normal operations.

SUMMARY OF THE INVENTION

These and other needs are addressed by the various embodiments and configurations of the present invention. In one aspect, the invention is directed to the combination of Raman spectroscopy, particularly surface enhanced Raman spectroscopy (SERS), and stroboscopic signal amplification (SSA).

This combination can have benefits. SSA can provide orders of magnitude signal enhancement over standalone, commercial-off-the-shelf (COTS) trace substance detectors. SSA is the use of a very short interval of broad-band light energy to momentarily create an enrichment of vapor and particulates above a sample surface. The enrichment of vapor and particulates can be collected for input to a detector. Using extremely short bursts of high energy, stroboscopic light, can increase the detection limits of traditional trace vapor detector systems by two or more orders of magnitude. As a result of the mechanism of SSA, the vapor mode detection of COTS instrumentation can sample both an increased vapor concentration and liberated micron-sized particles from the surface to be tested. Fine particulates are known to carry enhanced concentrations of contaminants, such as explosives. Employing stroboscopic enhanced detection can obviate the need to operate a detector in a tradition particle mode employing the manual steps of swiping a surface and placing the swipe in a pulsed thermal desorber. SERS has the added advantage of being able to identify substances via spectroscopic analysis, which is able to match chemical signatures to internal spectral libraries for conclusive identification, without requiring a gas phase separation, such as gas chromatography or ion mobility spectrometry.

In a first embodiment, a method includes the steps of:

(a) providing a, preferably textured, metal surface, the metal being a member of Group 11 (IB) of the Periodic Table of the Elements;

(b) contacting, in an irradiating chamber, a sample fluid with the metal surface, the sample fluid having a direction of flow at a first (preferably nonzero) angle relative to a plane of the textured metal surface;

(c) thereafter irradiating the textured metal surface with radiation to produce scattered radiation, the radiation having an optical path that is at a second angle relative to the plane of the textured metal surface, the second angle ranging from about 45 to about 90 degrees; and (d) analyzing, by a detector, the scattered radiation for spectral information associated with a target material.

In one configuration, the radiation is generated by a Raman excitation source in vicinity to the metal surface, and the scattered radiation focused on the end of a fiber optic also in close vicinity to the target surface. The fiber optic transmits the scattered radiation to a spatially dislocated detector, which analyzes the signals. This dislocation of the various components can reduce power requirements (due to reduced excitation loss from the laser passing through the fiber optic), reduce fiber optic induced fluorescence that must be filtered out before the radiation impacts the metal surface, and provide a robust and ergonomic design while addressing technical and safety requirements.

In a second embodiment, a method includes the steps of:

(a) forming, on the metal surface, a number of differing regions, each region being configured to adsorb differing target materials;

(b) contacting, in an irradiating chamber, a sample fluid with the metal surface;

(c) thereafter irradiating, with radiation, each of the differing regions to produce scattered radiation; and (d) analyzing, by a detector, the scattered radiation for spectral information associated with each of the target materials.

This embodiment can permit a single metal coating to adsorb multiple analytes, which can provide a highly versatile detection system.

In a third embodiment, a method includes the steps of:

(a) determining a reference signal, the reference signal being associated with an intensity of radiation scattered by the metal surface in the substantial absence of analytes being adsorbed on the surface and/or the reference signal being associated with an intensity of radiation scattered by a coating previously applied to the metal target;

(b) thereafter determining an analyte signal, the analyte signal being associated with an intensity of radiation scattered by analytes located on the metal surface;

(c) reusing the metal surface for multiple sample measurements; and (d) determining, for a selected current measurement, a ratio of the reference signal to an analyte signal and performing one or both of the following steps:

(i) determining, based on the ratio, a cumulative amount of analyte adsorbed on the metal surface in multiple prior measurements made using the metal surface and the selected current measurement;

(ii) determining, based on the ratio, a remaining operational life of the metal surface, the remaining operational life being related to an amount of active surface remaining in the metal surface; and (iii) setting a set of zero analyte spectral characteristics equal to spectral characteristics in the analyte signal for the selected measurement, wherein the zero analyte spectral characteristics are later differenced from second spectral characteristics in a second analyte signal to produce delta spectral characteristics, the second analyte signal being from a second measurement performed after the selected measurement, and wherein the delta spectral characteristics is used to detect the presence of additional analytes on the metal surface.

Using the ratio of the reference and analyte signals to assess analyte adsorption levels and remaining substrate life can provide increased measurement accuracy by reducing the likelihood of substrate overuse and substantially reduce operational costs through premature substrate replacement. The substrate can be interrogated in a fashion that shows a differential reading of the SERS signal over time but still allows absolute measurements to assess substrate life.

In a fourth embodiment, a system is provided that includes:

(a) an input for receiving a first sample to be tested;

(b) an output for outputting the first sample;

(c) first and second valves defining first and second flow paths, the first flow path bypassing the second flow path and the first and second flow paths being in fluid communication with the input and output;

(d) a strobe light positioned along the first flow path;

(e) a permeable sample contacting surface positioned along the first flow path;

(f) a detector positioned along the first flow path.

In a first operational mode, the first sample is passed along the first flow path and the strobe light is not activated, and, in a second operational mode, the first flow path is isolated from the input, the strobe light is activated, and a second sample derived from the porous sample contacting surface is processed by the detector.

This system can provide near real-time analyte detection. SERS instruments, while collecting data real-time, may require additional processing time to compare the spectral results to the internal libraries to identify the presence of an explosive chemical signature. Typically the processing time between taking a surface measurement until exact identification may take from 1 to 60 seconds depending on microprocessor speed. This processing time may be decreased with increased processing capabilities and does not slow the operator performance with respect to sampling multiple target surfaces in rapid succession.

In a fifth embodiment, a system is provided that includes:

(a) a plate to receive an item of footwear;

(b) first and second strobe lights to illuminate a footwear surface to be tested for a target material, the first and second strobe lights being positioned on either side of the footwear to be received by the plate and producing first and second samples;

(c) an irradiation chamber to receive the first and second samples; and (d) a detector to receive radiation contacted with the first and second samples.

The present invention can provide a number of advantages depending on the particular configuration. The invention can be designed as a very lightweight and agile hand wand for probing irregular and hard to access surfaces. The invention can provide fast sampling, data reduction, and reporting, have high sensitivity to trace substances, such as explosives and drugs, be specific as to analyte through the use of unique analyte markers, have a low cost, sample a wide variety of surfaces, and provide non-destructive detection. After a positive detection event, the metal-coated substrate can be preserved as evidence for a law enforcement proceeding. Because SERS substrates normally have a relatively uniform optical signature, the system is generally not required to be pre-calibrated for effective operation. Pre-calibration can be a time-consuming process.

These and other advantages will be apparent from the disclosure of the invention(s) contained herein.

As used herein, "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

"Deflagration" refers to a rapid autocombustion of particles of explosive as a surface phenomenon.

"Detonation" refers to a rapid, self-propagating decomposition of an explosive accompanied by a high-pressure-temperature wave that moves at about 1000 to about 9000 meters/second.

"Drugs" refer to a substance that acts on the central nervous system, e.g., a narcotic, hallucinogen, barbiturate, or psychotropic drug.

"Explosives" refer to a chemical compound, usually containing nitrogen, that detonate or deflagrate as a result of shock or heat.

The preceding is a simplified summary of the invention to provide an understanding of some aspects of the invention. This summary is neither an extensive nor exhaustive overview of the invention and its various embodiments. It is intended neither to identify key or critical elements of the invention nor to delineate the scope of the invention but to present selected concepts of the invention in a simplified form as an introduction to the more detailed description presented below. As will be appreciated, other embodiments of the invention are possible utilizing, alone or in combination, one or more of the features set forth above or described in detail below.

BRIEF DESCRIPTION OF THE DRAWINGS

FIG. 21A is a cross-section of a first operational mode of a testing system according to a fifth embodiment;

FIG. 21B is a cross-section of a second operational mode of the testing system according to the fifth embodiment;

FIG. 21C is a timing diagram of the fifth embodiment;

DETAILED DESCRIPTION

The Material Detection System

Figure 1:
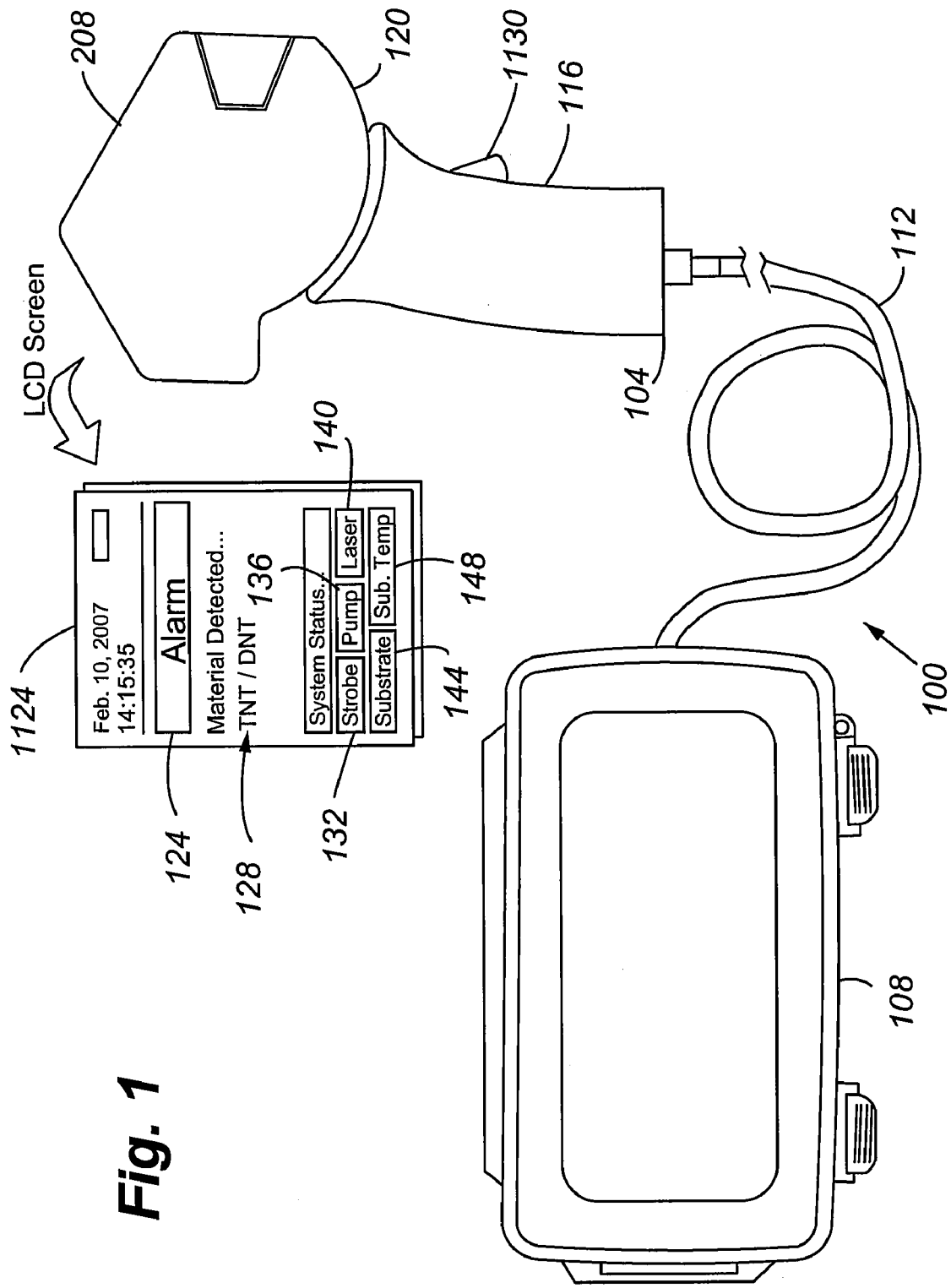
FIG. 1 is a material detection system according to a first embodiment.
Figure 2:
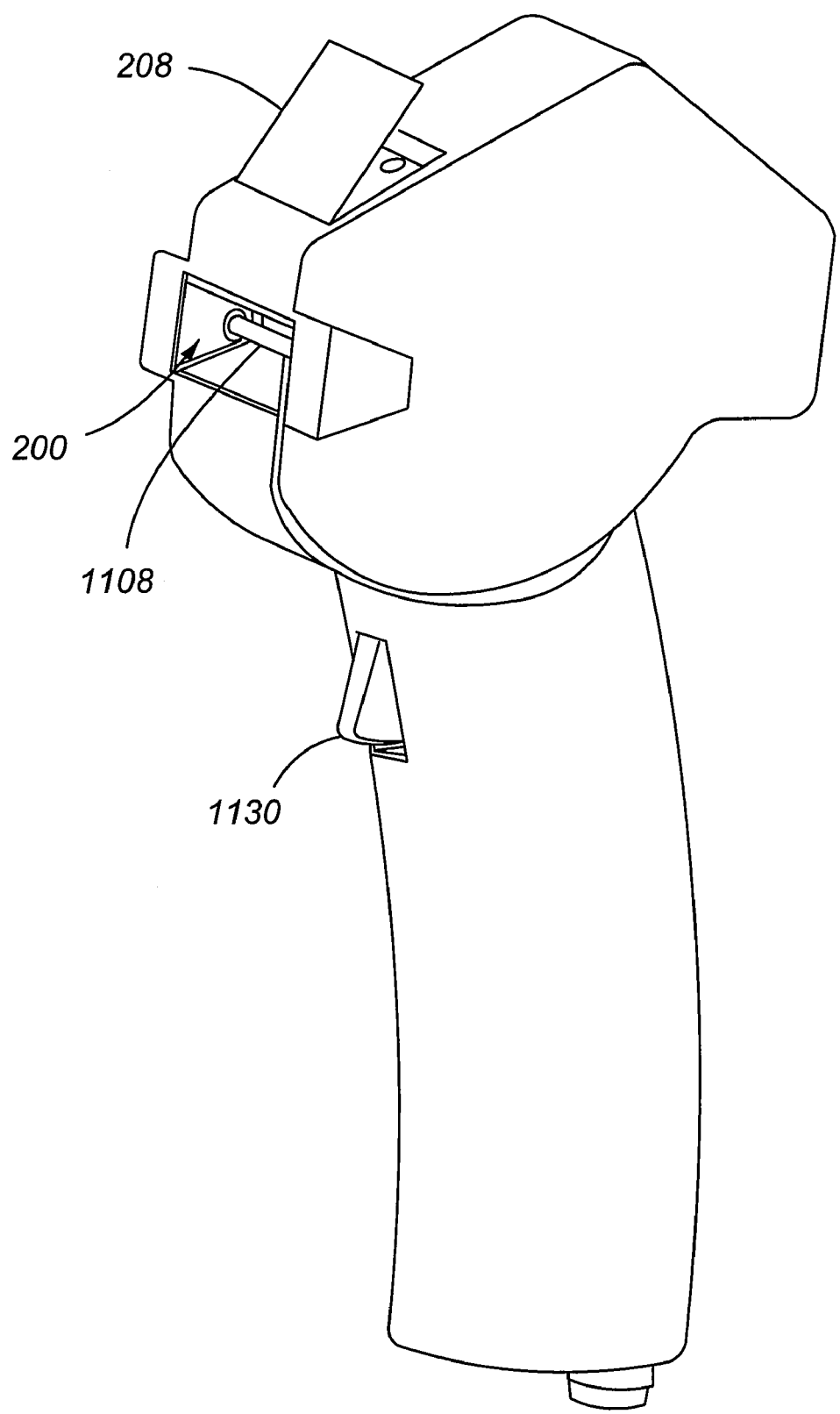
FIG. 2 is an isometric view of a handheld wand of the first embodiment.
Figure 3:
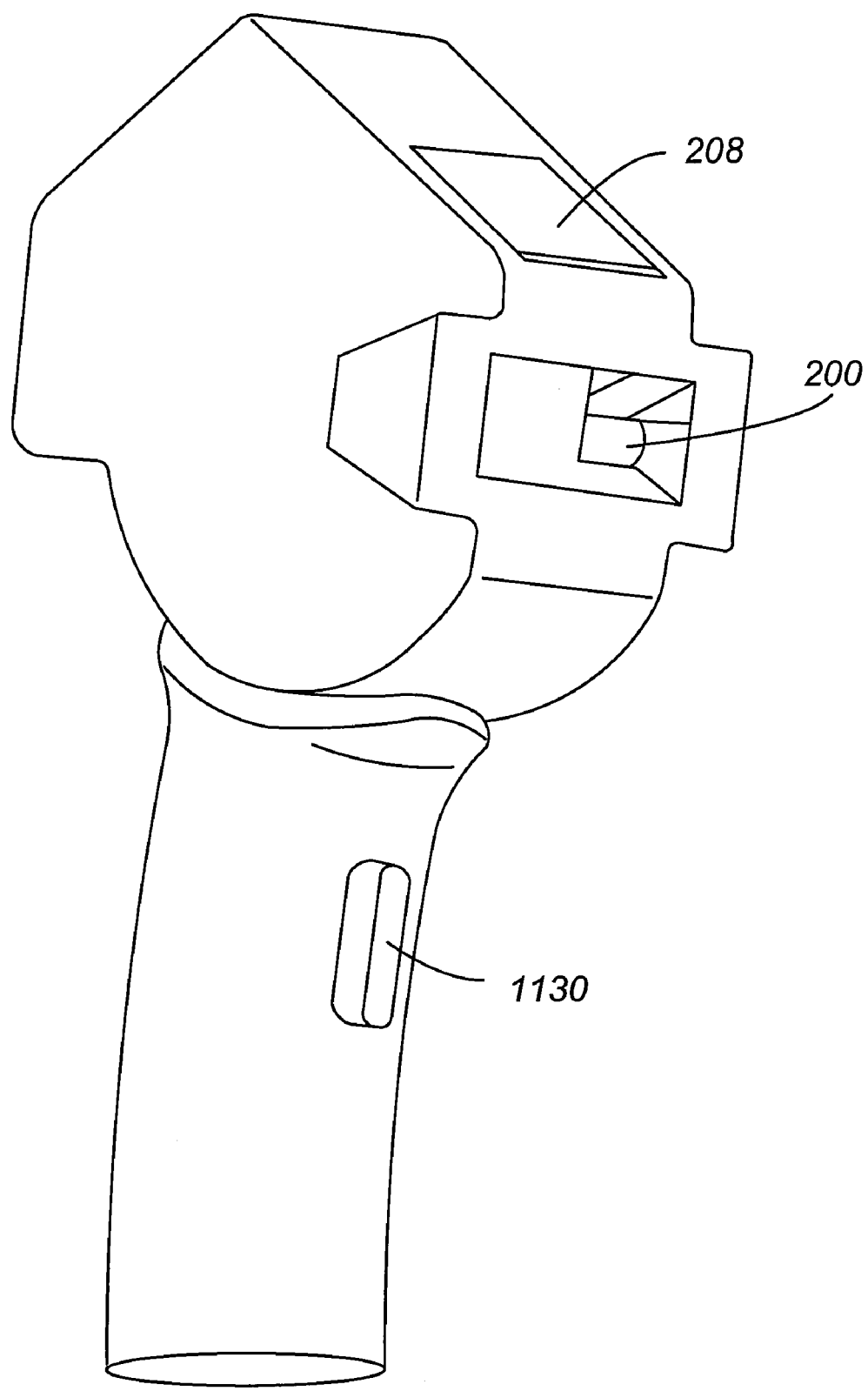
FIG. 3 is an isometric view of the handheld wand of the first embodiment.

With reference to FIGS. 1-11, a field-portable, material detection system 100 includes a hand wand 104 in electrical and signal communication via cable 112 with a user-carried pack 108. The wand housing 104 includes first and second housing portions 116 (handle) and 120 (head). As discussed below, the system 100 can combine Stroboscopic Signal Amplification (SSA) with Surface Enhanced Raman Spectroscopy (SERS). As will be appreciated, Raman detection methodologies other than SERS can alternatively or additionally be employed in the system 100.

The system can sample any surface, whether flowing or static, and detect any target material, whether air-, water- or soil-borne, or whether living or inanimate. In one configuration the target material is high boiling point and/or low vapor pressure substances and/or derivatives thereof and/or semi-volatile co-contaminant. Derivatives and co-contaminants can be unique markers to the presence of the source substance. Typically, a high boiling point material has a boiling point of at least about 150° C., more typically of at least about 250° C., and a low vapor pressure material is a material having a vapor pressure of no more than about $2 \times 10^{-3}$ mm Hg and more typically of no more than about $2 \times 10^{-4}$ mm Hg under conditions of standard temperature and pressure (STP). The derivative can itself be a high boiling point and/or low vapor pressure material. Typical substances of interest include at least one of an explosive compound, an explosive related compound, a chemical warfare agent, a drug, an industrial compound or toxic industrial compound (TIC), and derivatives thereof. Examples of target materials include explosives, such as TNT, nitroglycerine, ammonium nitrate, acetylides of copper and/or silver, mercury fulminate, lead azide, diazodinitrophenol, nitrosoguanidine, lead styphnate, cyclotrimethylenetrinatramine or RDX, pentaerythritol tetranitrate or PETN, triacetone triperoxide or TATP, dynamite, semtex, EGDN, DMNB, H-6, C-4, picric acid, nitrocellulose, and illicit drugs such as cocaine, heroin, opium, marijuana, methamphetamines, LSD, and co-contaminants from the manufacturer or purification of these drugs. Examples of TNT derivatives that may act as a unique marker include dinitrotoluene, 2-ADNT and 4-ADNT.

The sample area is commonly an animate or inanimate surface. Examples of sample areas include the skin of a body part, such as a hand, clothing, shoes, documents including travel documents, currency, weapons and weapon components, vehicles and vehicle components, luggage, bags, mail, packages, envelopes, metal, glass, plastic and painted surfaces, refuse, biological or biological related matter, vehicles, cargo containers, furniture surfaces, flooring, wood and canvas.

Figure 11:
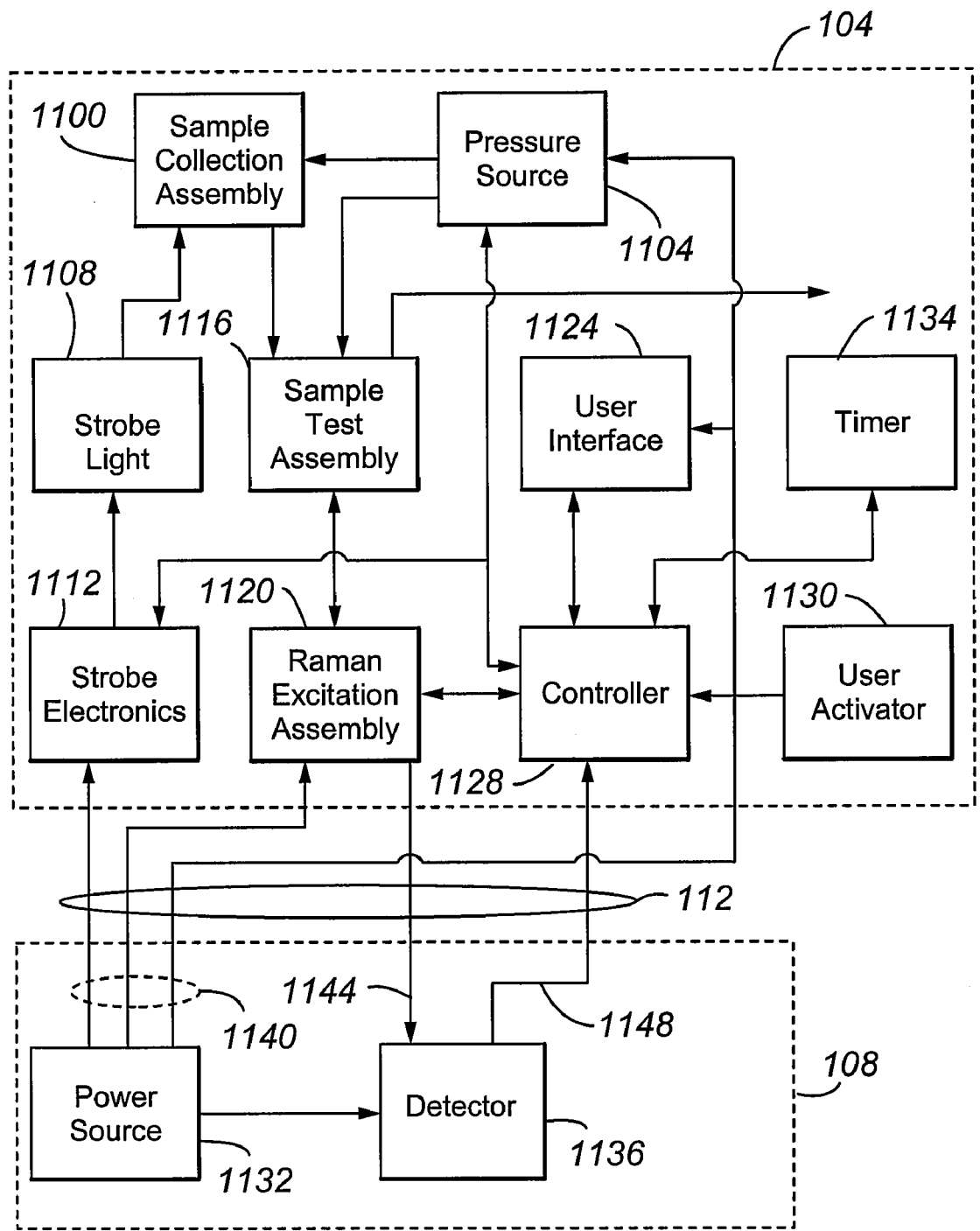
FIG. 11 is a functional block diagram of the handheld wand of the first embodiment.

With reference to FIG. 11, the system 100 includes a number of subcomponents. The hand wand 104 includes a sample collection assembly 1100 for collecting and handling the sample, a pressure source 1104 to provide the negative pressure to draw the sample into the sample collection assembly 1100, a strobe light 1108 and strobe electronics 1112 to irradiate and mobilize the target material in the sample, a sample test assembly 1116 to test the collected sample, a Raman excitation assembly 1120 to provide radiation of a selected wavelength to the test assembly 1116 for sample testing, a user interface 1124 to receive input from and provide audible and/or visual output to the user, a controller 1128 to control the various subcomponents, analyze data, and execute other software algorithms, and an activator 1130 to initiate a sample collection and measurement cycle. The pack 108 includes a power source 1132 and a detector 1136 (e.g., a spectrophotometer (spectrometer)) 1136. The cable 112 includes power cabling 1140 to supply power to the strobe electronics 1112, Raman excitation assembly 1120, pump 1104, user interface 1124, and controller 1128, fiber optic transmission line 1144 to receive scattered radiation from the sample test assembly 1116 and Raman excitation assembly 1120, and signal line 1148 to receive control signals from the controller 1128 to the detector 1136 and provide control and data signals from the detector 1136 to the controller 1128. As will be appreciated, the scattered radiation will include a surface enhanced Raman scattering of any target substances on the SERS substrate assembly.

In this embodiment, the heaviest components, namely the power source 1132 and detector 1136, are located in the pack 108 that can easily be affixed to a body part of the operator, thereby maintaining body center of mass stability. The pack 108 is preferably configured as a pack positioned on the user's torso, as a belt attachment, or as a hand carried unit. This configuration can provide, relative to prior art eTED units, increased levels of ergonomics for the user.

With reference to FIGS. 1-11, the sample collection assembly 1100 includes a trapezoidal shaped strobe housing 200 and a sample inlet conduit 204. As will be appreciated, the housing 200 can have any desirable shape. In one configuration, the conduit 204 is unheated to reduce the power requirements for the system 100. This is possible because the length of the conduit 204 is relatively short and the pressure, and resulting sample velocity, relatively high. Commonly, the length of the conduit 204 is no more than about 3 cm and even more commonly ranges from about 1 to about 2 cm while the absolute value of the pressure measured at the pump inlet 500a is at least about 30 torr below ambient atmospheric pressure and even more commonly ranges from about 5 to about 200 torr below ambient atmospheric pressure. In another configuration, the conduit 204 is heated to inhibit condensation of the target material in the conduit 204. In either configuration, the conduit 204 includes a material that will deter target material deposition, such as silcosteel-treated stainless steel.

Figure 4:
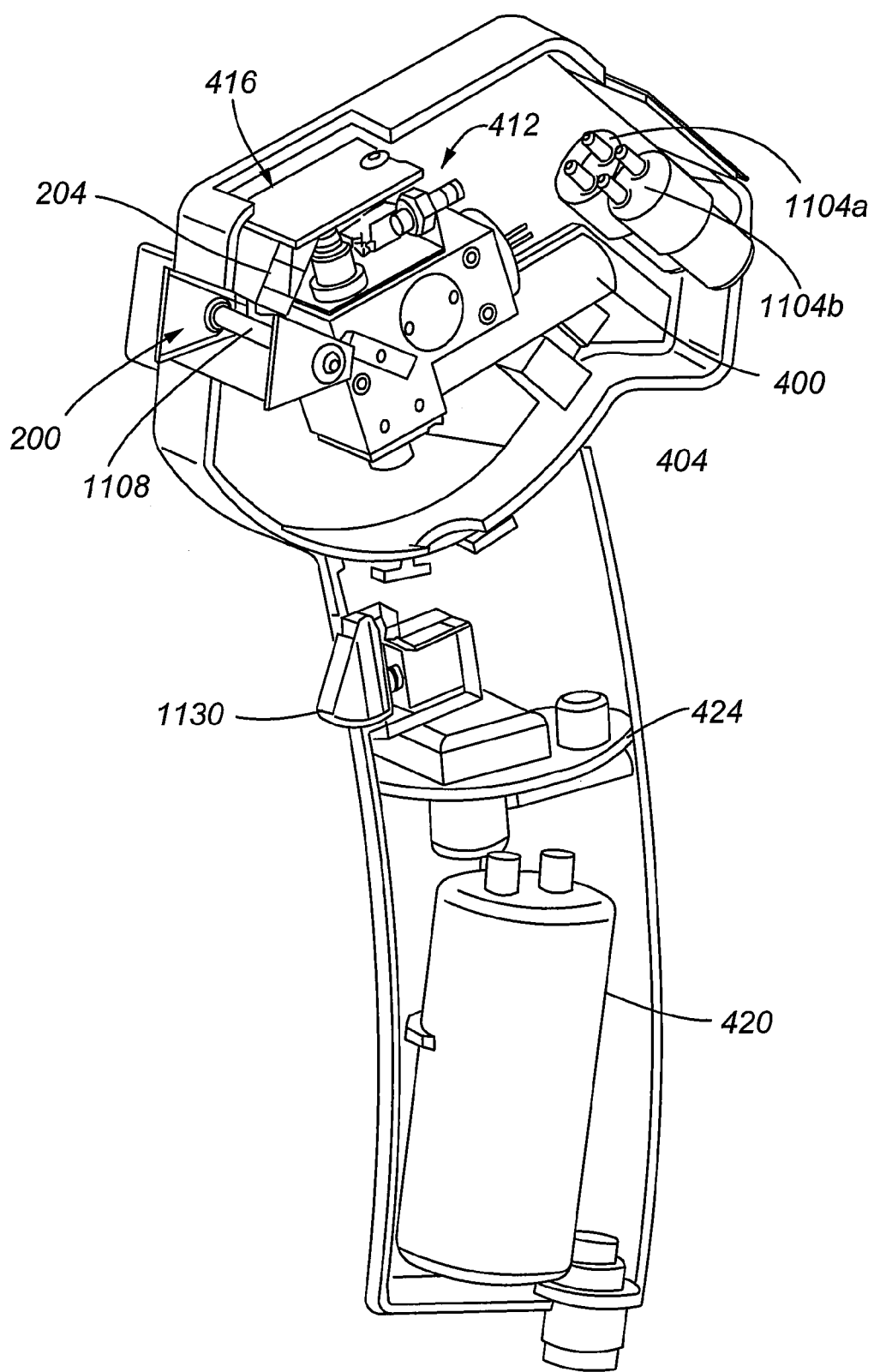
FIG. 4 is a first cross-sectional view of the handheld wand of the first embodiment.
Figure 5:
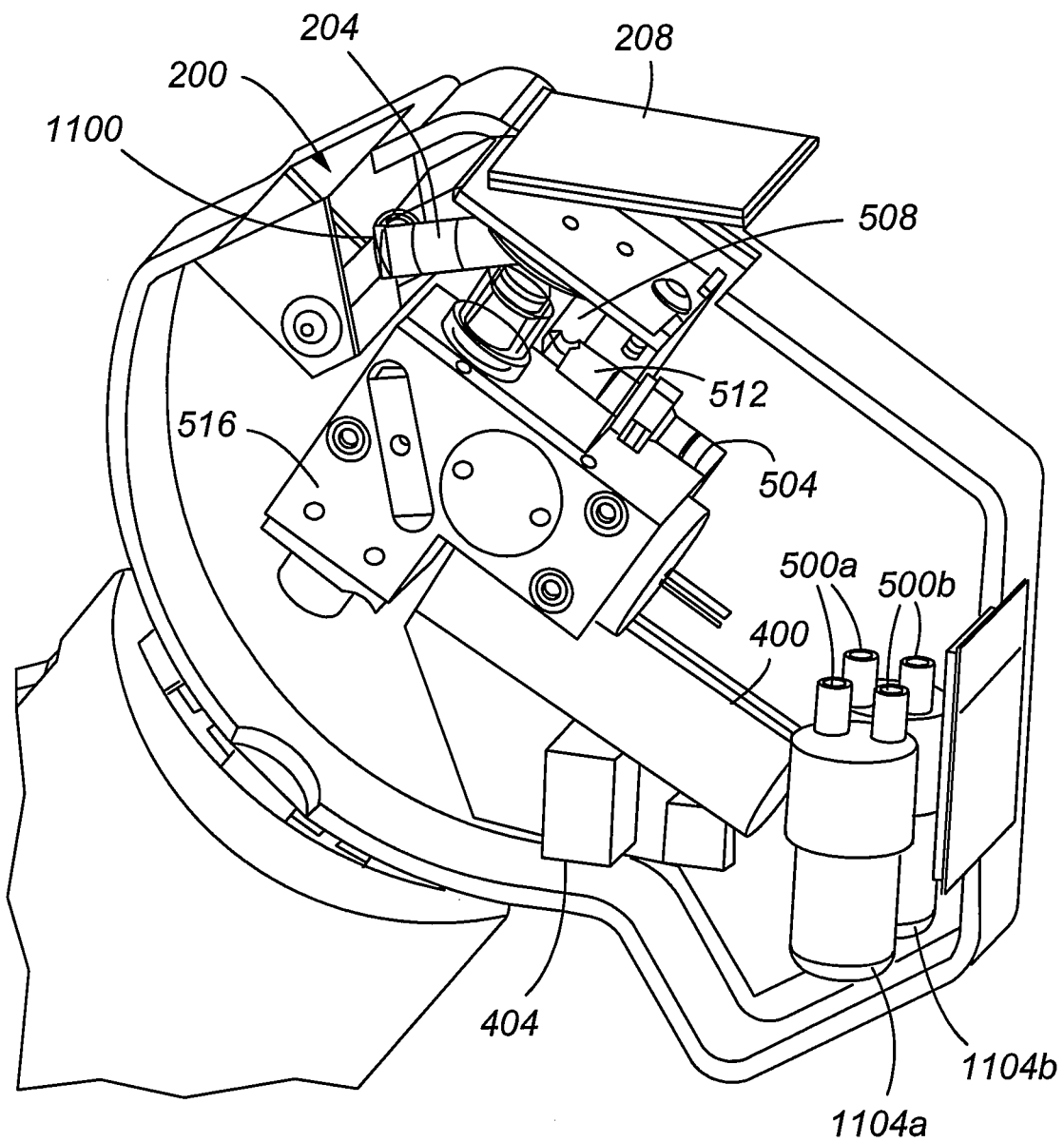
FIG. 5 is a second cross-sectional view of the handheld wand of the first embodiment.
Figure 6:
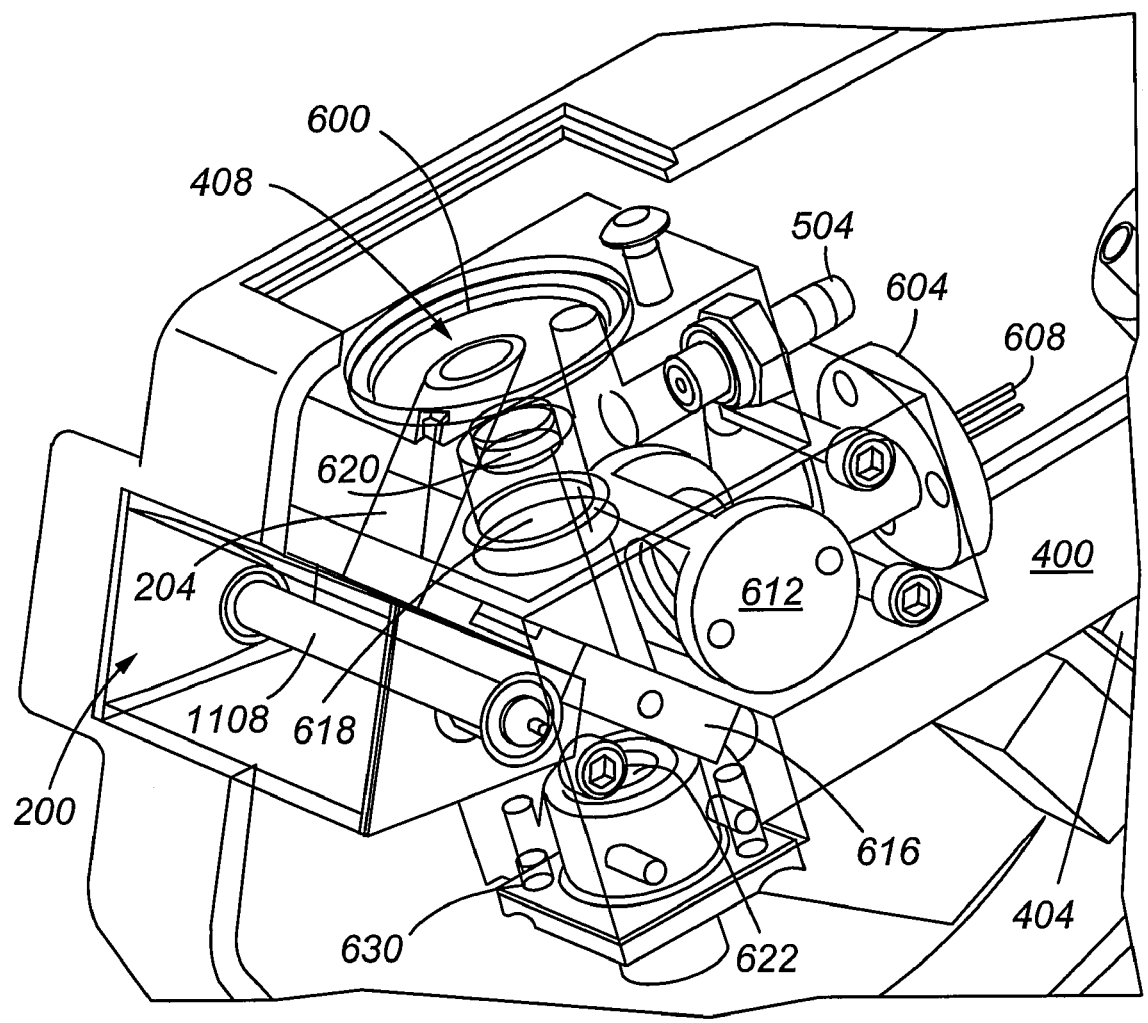
FIG. 6 is a third cross-sectional view of the handheld wand of the first embodiment.
Figure 7:
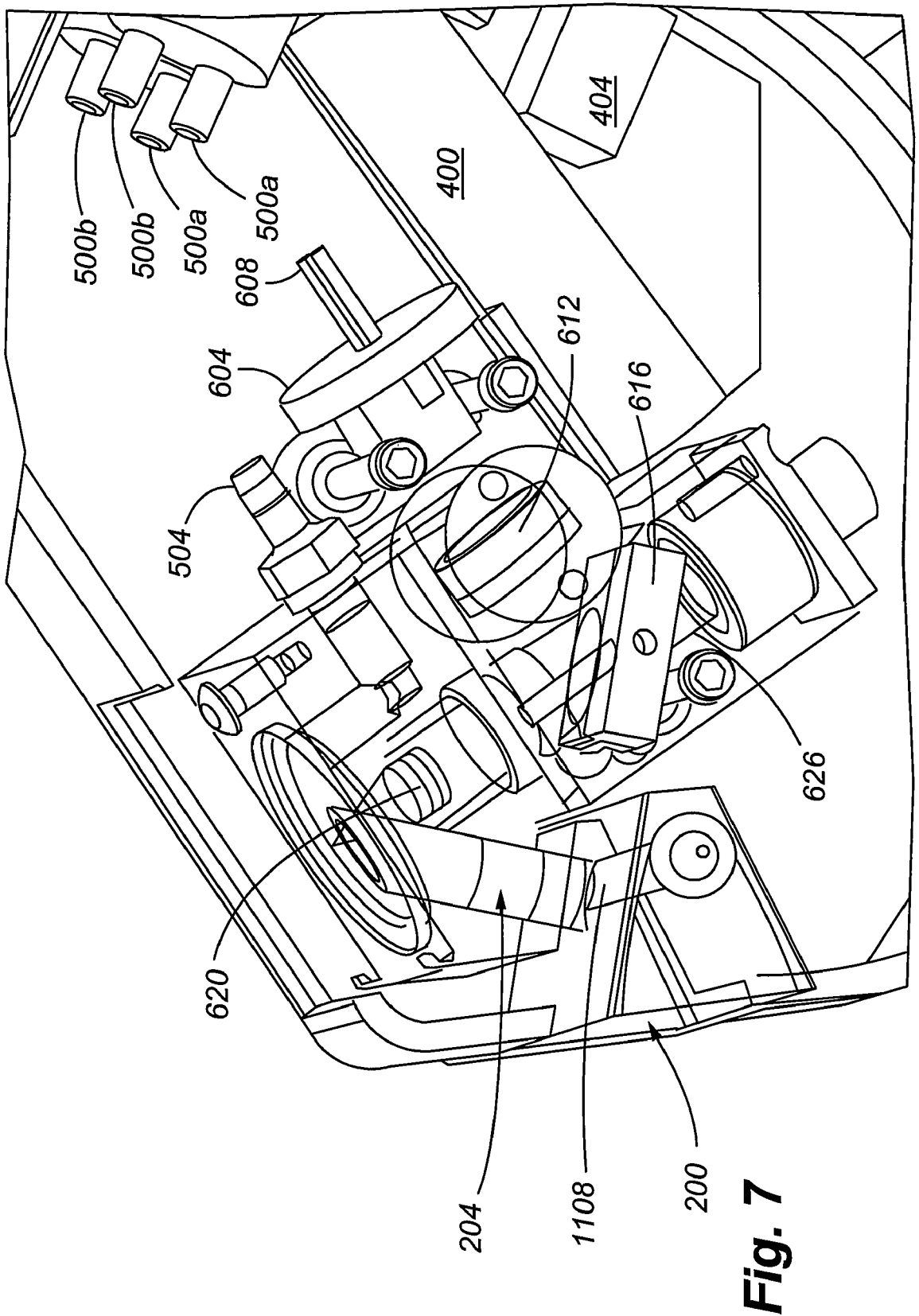
FIG. 7 is a fourth cross-sectional view of the handheld wand of the first embodiment.

The pressure source 1104 can be any suitable vacuum pump or positive pressure source, such as a fan or blower. The pressure source 1104 can be one or multiple pressure sources. While the pressure source 1104 will hereinafter be described as a vacuum pump, it is to be understood that it can be configured as one or more positive pressure sources. FIGS. 4-5 show first and second vacuum pumps 1104a, b. The projections 500a, b extending from each pump represent inlet and outlet lines, with the inlet line 500a of each pump being connected to the sample outlet 504 from the sample test assembly 1116 and the outlet line 500b being connected to an exhaust (not shown) to the ambient atmosphere.

The strobe light 1108 uses extremely short bursts of energy light to desorb stroboscopically target materials. For effective low vapor pressure and particle desorption, a desired minimum energy at the sample surface is commonly about 0.4 J/cm$^2$. Such energy per unit surface area value provides significant increase in the concentration of airborne compounds and/or particles from the sample, as compared to using a detector without strobe signal amplification. In terms of energy per area per time to peak discharge, that is, the initial time it takes for the strobe to go from zero to peak illumination flux, the typical value is about 6 mJ/cm$^2$/μs, calculated as 0.4 J/cm$^2$ divided by 60 μs, where, in one embodiment, the peak illumination flux time is about 60 μs. However, embodiments of the present invention may operate with a time to peak discharge as low as about 5 μs, thereby yielding about 80 mJ/cm$^2$/μs (calculated as 0.4 J/cm$^2$ divided by 5 μs) for the energy per area per time to peak discharge. As defined herein, the "time to peak discharge" or "rise pulse" means the duration of moving from zero illumination to maximum illumination where the sample surface and substrate are absorbing radiant energy.

The strobe electronics 1112 include suitable circuitry for power up and discharge. Examples of strobe electronics 1112 include capacitors 400 and 420, and circuit board 424.

The sample test assembly 1116 includes an irradiating chamber 408, an outlet assembly 412, and a SERS substrate assembly 416. The irradiating chamber 408 is disc-shaped as defined by a circular cavity 600 in a sample housing 1012 and the SERS substrate assembly 416. The housing is preferably fabricated from a light absorbtive material, such as black Delrin or black anodized aluminum, to absorb at least most, if not all, of the reflected and scattered light. The outlet assembly 412 includes orthogonally oriented first and second conduits 508 and 512 and sample outlet 504. SERS substrate assembly 416 includes a chip 1000 and supporting substrate 1004. This assembly is discussed in more detail below. While the invention is described herein with reference to a SERS substrate assembly, it is to be understood that optical detection techniques other than SERS may be employed by the present invention.

The second housing portion 120 includes a hinged access door 208 to provide access to the SERS substrate assembly 416. The substrate assembly 416 includes first and second connectors 1008a,b, which removably attach the substrate assembly 416 in the chamber 408. To prevent radiation exposure of the user, when the access door 208 is opened, the Raman excitation assembly 1120 is deactivated, such as by an interlock switch. An example of an interlock switch is a Hall effect switch. As will be appreciated, a magnet would engage the access door to break the Hall effect sensor when the door is opened. The interrupted Hall effect sensor would act as an open switch in the power line to the Raman excitation assembly, thereby preventing the power source 1132 from powering the Raman excitation assembly 1120. Other switch configurations can be envisioned by one of ordinary skill in the art.

The Raman excitation assembly 1120 is surrounded by an "L"-shaped housing 516 and, in one configuration, includes a laser 604 having power leads 608 connected to the power source 1132, a first steering lens 612 that collimates the laser light, a beam splitter 616 (e.g., a half-silvered beam splitter or other type of beam splitter) that reflects substantially all of the collimated laser light along optical path 618 while passing substantially all scattered light passing along the optical path 618, and a second concentrating lens 620 that focuses the laser light onto an active area of the SERS substrate assembly 416. The scattered light is collimated by the second concentrating lens 612, passes through the beam splitter 616, along optical path 626 to a third concentrating lens 622, which focuses the scattered, collimated light onto the fiber optic 1144 (not shown), which is received by the housing 630. The second and third lenses 620 and 622 are concentrating lenses that (depending on the direction of travel through the lens) convert a divergent beam into a collimated beam and a collimated beam into a convergent beam. As will be appreciated, the lenses 620 and 622 can be simple or compound lenses, depending on the application. Although the wavelength spectrum of the Raman excitation source is selected based upon the target materials to be detected, the source is normally selected such that at least most of the laser light has a wavelength in the range of about 5320 to about 10640 Angstroms and even more commonly of about 7850 Angstroms. Although the Raman excitation source is discussed with specific reference to a laser, it is to be understood that the source may be any other radiation source capable of providing radiation of the desired wavelength and intensity.

In one configuration the laser 604 is a laser light emitting diode (LED). Laser LEDs are available in a range of wavelengths from the visible into the infrared. Therefore, a LED with the most effective wavelength to provide Raman scattering for the target material is preferably used. Pulsed LEDs are available with a power of up to 50 W or more. The pulse time is on the order 50 ns. Laser LEDs are small, easily manipulated and operate at low voltages, typically at 12V. In a continuous mode, laser LEDs draw low currents of a few tens of milliamps. Thus, in accordance with embodiments of the present invention, a laser LED may be easily incorporated into the hand wand.

The user interface 1124 is typically a Light Emitting Diode (LED) and/or Liquid Crystal Display (LCD) graphical display that may or may not have user selectable inputs to permit the user to provide commands to the system 100. An example of a user interface 1124 is provided in FIG. 1. The display includes the date (Feb. 10, 2007 at 14:15:35), an alarm indicator 124 that is illuminated when a target material is detected, a description 128 of the material detected (shown as being TNT/DNT), and various system status indicators, namely the status indicator 132 of the strobe, the status indicator 136 of the pump, the status indicator 140 of the laser, the status indicator 144 of the substrate, and the status indicator 148 of the substrate temperature. The indicators are illuminated when a problem is detected with the respective component.

The controller 1128 can be any processor or microprocessor and includes memory. The controller 1128 monitors and controls the operations of the various system components, provides alarms for system malfunctions, receives and implements user commands, and analyzes data collected by the detector 1136 and provides appropriate output to the user. The controller firmware and memory is located on circuit board 404.

The user activator 1130 is a switch assembly that, when activated by the user, causes initiation of the sample collection and measurement cycle. This cycle activates the strobe 1108 to mobilize the sample, the pumps 1104a,b to collect the mobilized sample, the Raman excitation assembly 1120 to irradiate the collected sample, and the detector to analyze the scattered radiation.

The power source 1132 can be any suitable power source capable of meeting the power requirements of the system 100. Typically, the power source includes one or more batteries, though a renewable energy source, such as solar energy, or the power grid may be used.

Although the detector can be any device suitable for detecting a Raman scattering of a target material, the detector 1136 is commonly a photometer (e.g., a device for measuring light intensity) that can measure intensity as a function of the color, or more specifically, the wavelength of light. The spectrometer can be any suitable type of spectrophotometer that is capable of processing the wavelength range of the scattered light. Other distinctions among spectrophotometers are the wavelengths they work with, the measurement techniques they use, how they acquire a spectrum, the sources of intensity variation they are designed to measure, and their spectral bandwidths and linear ranges.

Figure 8:
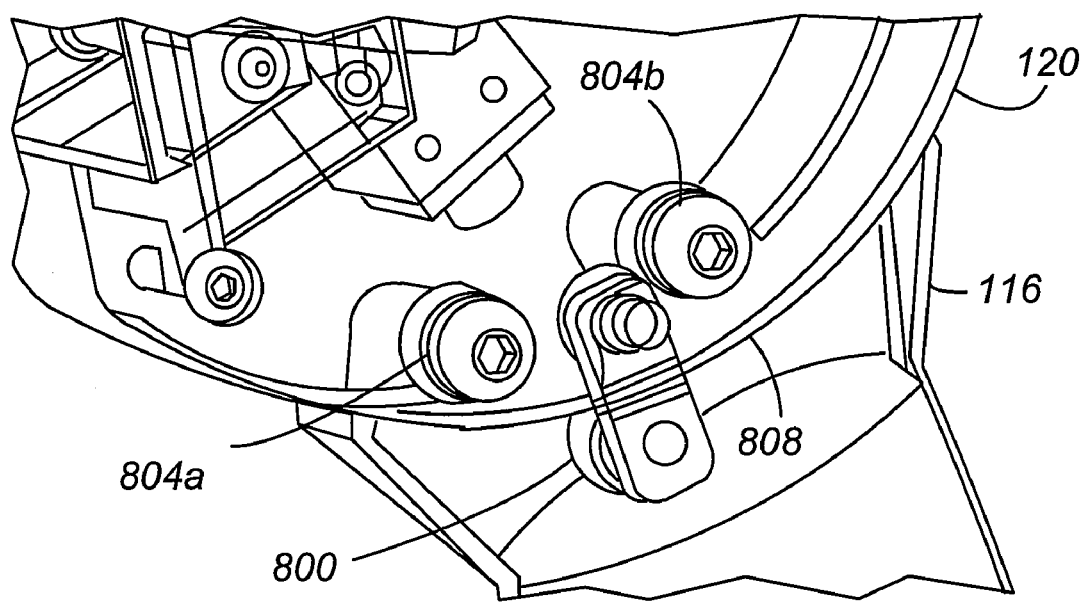
FIG. 8 is a fifth cross-sectional view of the handheld wand of the first embodiment.
Figure 9:
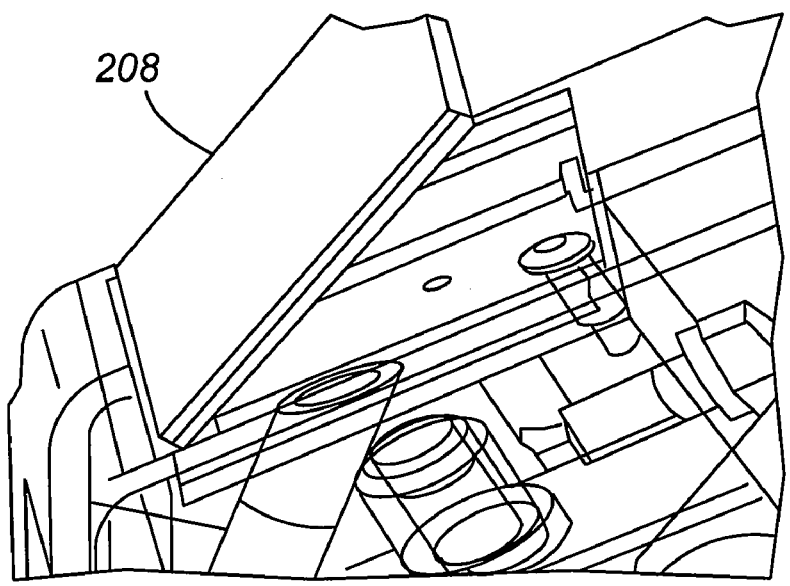
FIG. 9 is a sixth cross-sectional view of the handheld wand of the first embodiment.
Figure 10:
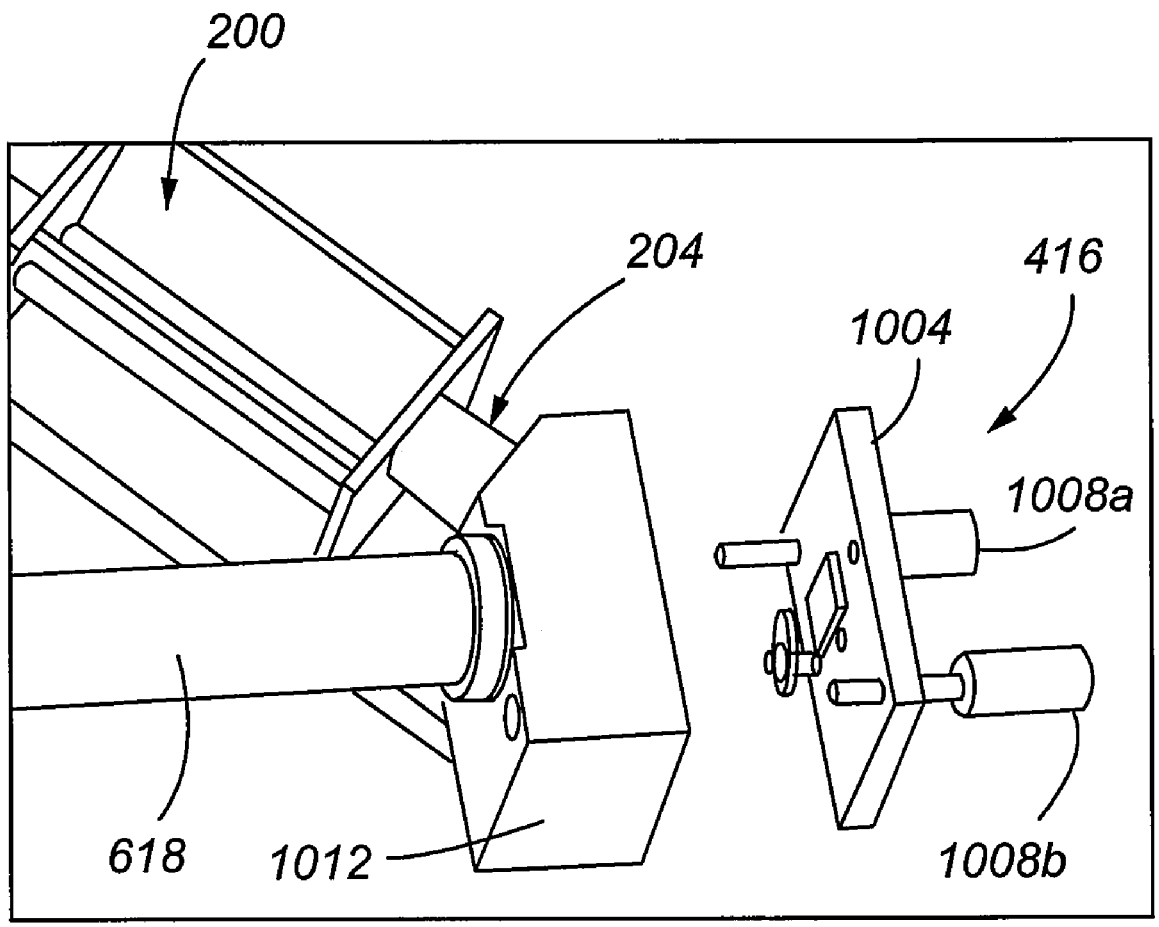
FIG. 10 depicts a partially disassembled view of selected components of the handheld wand of the first embodiment.

With reference to FIG. 8, the first and second housing sections 116 and 120 are rotatably disposed relative to one another to permit the strobe 1108 to be conveniently directed by the user towards the surface to be sampled. As shown in FIG. 8, a bearing 800 in the first housing section 116, or handgrip, and bearings 804a,b in the second housing section 120, or head, slidably engage an adjacent housing surface along the joint 808 to facilitate both attachment and movement. As will be appreciated, other means of realizing the pivot, or rotatable engagement, do not use bearings. The head is typically not pivoted frequently during use and should not pivot unless forced to move. The large area of engagement between the head and the handle will absorb substantial impact without damage to the joint 808. Typically the length of the joint 808 ranges from about 20 to about 40% of the head circumference.

As can be seen from FIG. 11, the Raman excitation assembly 1120 and the detector 1136 are not co-located but are located in separate, discrete housings. Compared to eTEDS units of the prior art, this configuration can permit the use of a lower power laser, because there will not be any excitation loss due to the laser passing through the fiber optic 1144. Additionally, there will commonly not be any fiber optic induced fluorescence that must be filtered out before the laser light impacts the SERS substrate assembly 416.

Figure 15:
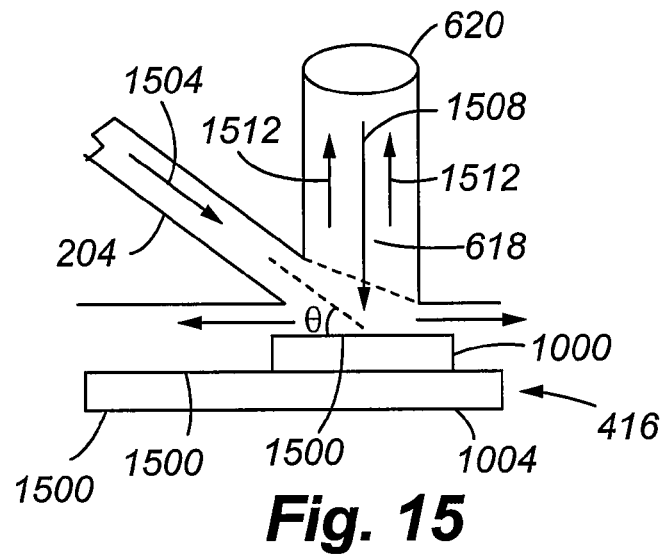
FIG. 15 depicts a cross-section of an optical system according to a fourth configuration.

Referring to FIG. 15, the configuration of the Raman excitation assembly 1120 will now be discussed. The inlet 204 for sample 1504 is at an angle 45° (which preferably ranges from about 25 to about 65° and more preferably is about 45°) with respect to the planes 1500 of the SERS substrate assembly 416. This orientation allows the Raman laser light 1508 and scattered light 1512 to remain at least substantially normal or orthogonal (i.e., at about 90°) relative to the planes 1500 of the SERS substrate assembly 416 (or to the plane of the active surface of the chip 1000), which can be an important parameter for successful SERS operation. Due to the desire to maintain a short and non-turbulent path between the strobe light 1108 and the SERS substrate assembly 418, this configuration can be highly advantageous.

Because the sample 1504 is normally not applied deliberately to the SERS substrate assembly, the sample 1504 should contact the substrate in a manner to provide an enhanced signal-to-noise ratio. When the analyte interacts with the chip surface of the SERS substrate assembly, it is attracted to the surface through chemical adsorption, either through van der Waals forces or an architected chemical affinity (e.g., as ion oxides attracting arsenic and antibodies attracting bacteria). For effective detection of a target material, the target material must adsorb, or otherwise attach, within about 20 nm of a nano-textured metal from Group 11 (IB) of the Periodic Table of the Elements (particularly gold) surface that is formed, such as in a layer or coating, on the chip 1000.

In one configuration, the adsorption is realized using a SERS substrate manufactured under the tradename Klarite® by Mesophotonics Limited or manufactured by Inphotonics. Klarite®, features a systematically designed nanometer scale surface patterning in silicon that is coated with gold. Klarite® can provide up to a $10^6$ increase in Raman signal.

In another configuration, the adsorption is realized using an organic thiol coated metal substrate through a process known as a Self-Assembled Monolayer (SAM). In SAM, a thiol, such as 1-propanethiol, is combined with an alcohol solvent, such as ethanol, and applied to the active metal surface for a time sufficient for formation of a SAM monolayer over the entire active metal surface. After monolayer formation, the coated metal surface is rinsed in another alcohol, such as methanol, to remove excess thiols. While not wishing to be bound by any theory, it is believed that the thiol end adheres, by some mechanism, to the nano-textured metal surface. The other (free or unattached) thiol end can be tailored to be any of a number of active groups, such as metal oxides, organic groups, antibodies, and/or aptamers. As an example, the active group iron or titanium oxide attracts and adheres to heavy metals, organic active groups can be tailored to attract and adhere to targeted organic compounds, and antibodies or aptamers can be tailored to attract and adhere to targeted biological organisms.

Organic thiols are particularly attractive as a coating due to the strong, irreversible attraction of the sulfur functionality to the metal surface. This attraction can passivate the underlying nano-textured metal surface, thereby allowing the metal to retain its electromagnetic enhancement to the nearby adsorbed analyte over periods of time in excess of months or even years. The attraction can also enhance the ability to assess temporal variations and age-induced degradation of the system optical performance, such as related to laser output and detector detection quantum efficiency.

Figure 19:
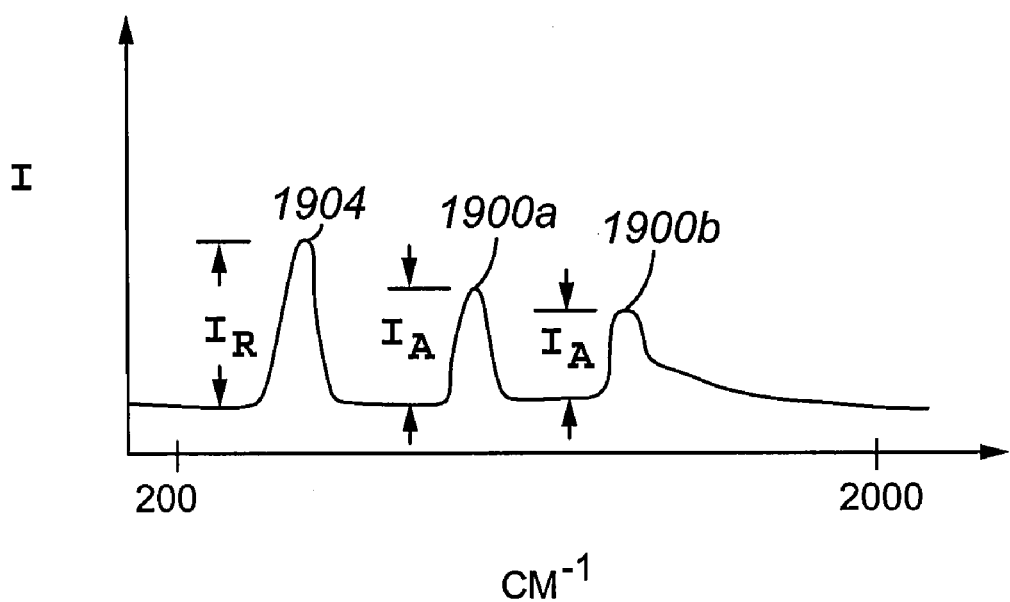
FIG. 19 is a plot of intensity ("I") (vertical axis) against wave number ($cm^{-1}$) (horizontal axis)

The use of a SAM thiol coating reference signal to calibrate the target analyte signal and estimate the remaining operational life of the metal surface on the SERS substrate assembly will be discussed with reference to FIG. 19. The Raman reference signal intensity from the coating is denoted $I_R$ and the signal(s) from the analyte is/are denoted $I_A$. In the case where the analyte presents more than one Raman peak 1900*a,b*, or when there is more than one analyte, the total signal may be integrated over all of the relevant Raman peaks 1900*a,b* and 1904 as noted in the equation below:

$$I_A = \sum_{j=1}^{n} I_{A_j}$$

where "j" represents the signal for each analyte peak. Since the coating concentration under the area excited by the laser remains constant the signal $I_R$ will remain constant. Thus as analyte is adsorbed onto the SERS substrate the ratio of $I_A$ to $I_R$ will provide a basis for determining the cumulative amount of analyte adsorbed on the substrate over time.

The same Raman signal from the coating may be used in comparison to the analyte Raman signal to assess the remaining operating life of the Raman substrate; that is, when $I_A$ is at a certain threshold level with respect to $I_R$ the substrate is deemed to be ready for replacement. As illustrated by the above equation, normal operation of the eTEDS system 100 will examine the change in the Raman signal during each sample collection and analysis cycle. Each cycle represents the passing of a new sample across the SERS substrate assembly, and it is the signal introduced by this single sample that is the event of interest, not the total accumulation of analyte on the substrate over all of the events. There may, however, be operational modes where the total accumulation over multiple events will be of interest and even these analytical modes may not start from a "clean" point of observation but rather may start from a point of observation where there is already analyte present from prior cycles that produced a previous signal that is called a zero analyte signal. This delta signal, $\delta I_A$, is the signal that is used to make decisions for a positive occurrence of target analytes. The delta signal is the difference of the zero analyte signal from the current signal, $I_A$. However, the total signal, $I_A$, of the analyte (or multiple analytes) with respect to the reference signal $I_R$ will be an indicator of the degree of active surface remaining on the SERS substrate, and this an indication of whether the substrate will soon fall out of calibration or utility for adsorbing new analyte.

Figure 26:
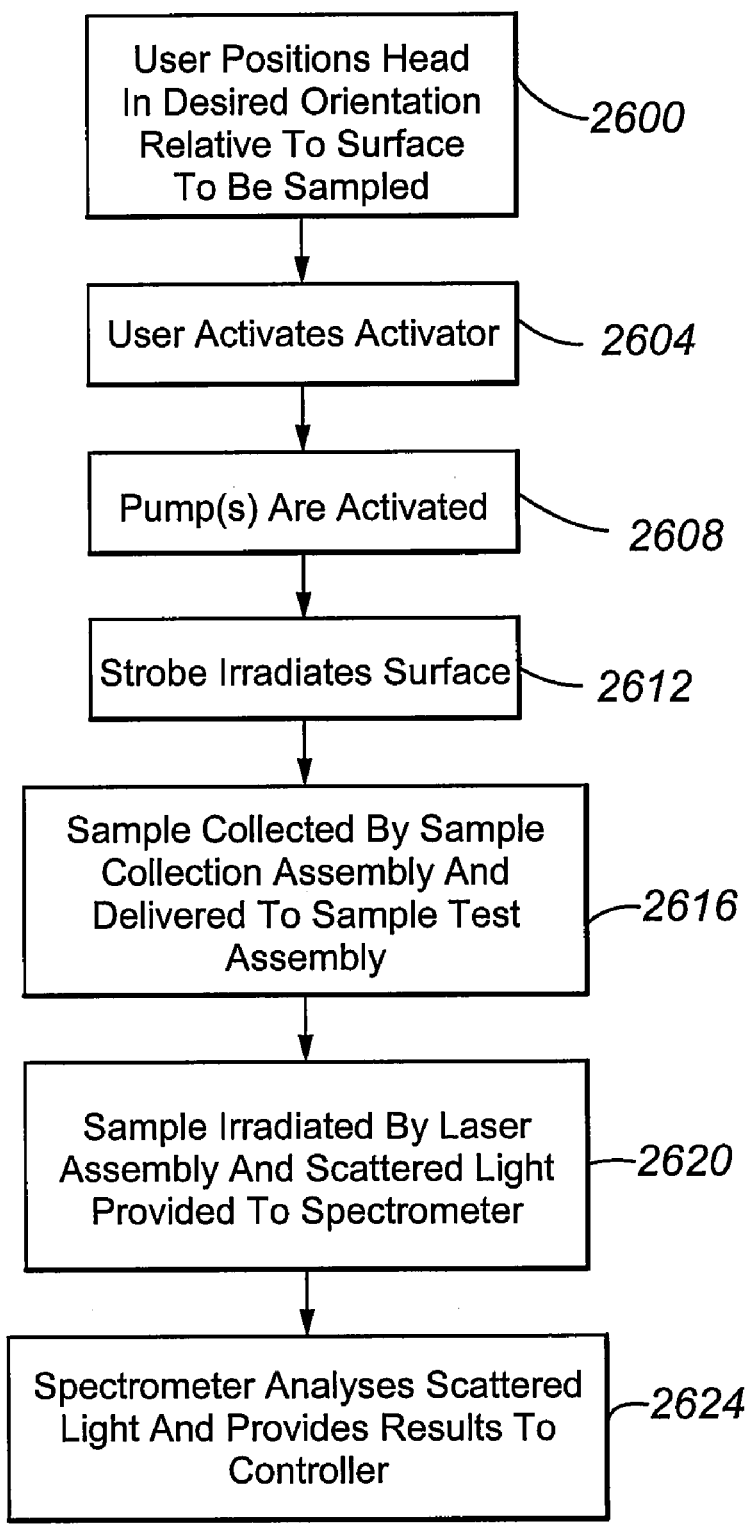
FIG. 26 is a flow chart depicting a method of operating the first embodiment.

The operation of the system 100 and controller 1128 will now be discussed with reference to FIGS. 26-27.

In step 2600, the user positions the strobe light 1108 in the head 120 in a desired orientation relative to the surface of the object to be sampled.

In step 2604, the user, while holding the head in the desired orientation, activates the user activator 1130 to initiate a sample collection and analysis cycle.

In response, the pumps, in step 2608, are activated to begin drawing in a sample in spatial proximity to the surface. Commonly, the pumps remain activated for a selected time after a cycle is completed in the event that the user immediately initiates another cycle.

In step 2612, the strobe light 1108 irradiates the surface to liberate a target material, if present. In one configuration, the strobe light 1108 is initiated after a selected time following user activation of the activator 1130.

In step 2616, the sample is collected by the sample collection assembly 1100 and delivered to the sample test assembly 1116. In the sample test assembly 1116, the sample contacts the SERS substrate assembly and any target material in the sample is adsorbed onto the nano-textured metal surface on the chip 1000.

In step 2620, the collected sample is irradiated by the Raman excitation assembly 1120 and scattered light is provided, via the cable 112, to the detector 1136. As in the case of the strobe light 1108, the Raman excitation assembly 1120, in one configuration, is activated a selected time after a cycle is initiated.

Surface enhanced Raman spectroscopy (SERS) has been shown to be able to extend the sensitivity of Raman spectroscopy from 1% (10,000 ppmv) bulk gaseous detection to low ppb concentrations for trace vapor detection. The Raman enhancement comes from the increase of the local optical field intensity within nano-textured metals of Group 11 (IB) of the Periodic Table of the Elements [i.e., Au, Ag, Cu] and in the nano-scale gaps between colloidal particles and/or surface roughness. Increases in the intensity of the Raman signal are regularly observed to be on the order of $10^4$ to $10^6$ and can be as high as $10^8$ to $10^{14}$.

While not wishing to be bound by any theory, there are two primary mechanisms described in the literature to explain the SERS signal enhancement, namely electromagnetic enhancement (EME) and chemical enhancement (CE). The electromagnetic effect is believed to be the dominant effect while the chemical effect is believed to contribute only one or two orders of magnitude enhancement. The EME is dependent on the presence of the metal surface's roughness features, while the CE involves changes to the adsorbate electronic states due to chemisorption of the analyte.

In step 2624, the detector 1136 analyzes the scattered light and provides the results to the controller 1128. The scattered light includes surface enhanced Raman scattering of any target material on the SERS substrate assembly.

Figure 27:
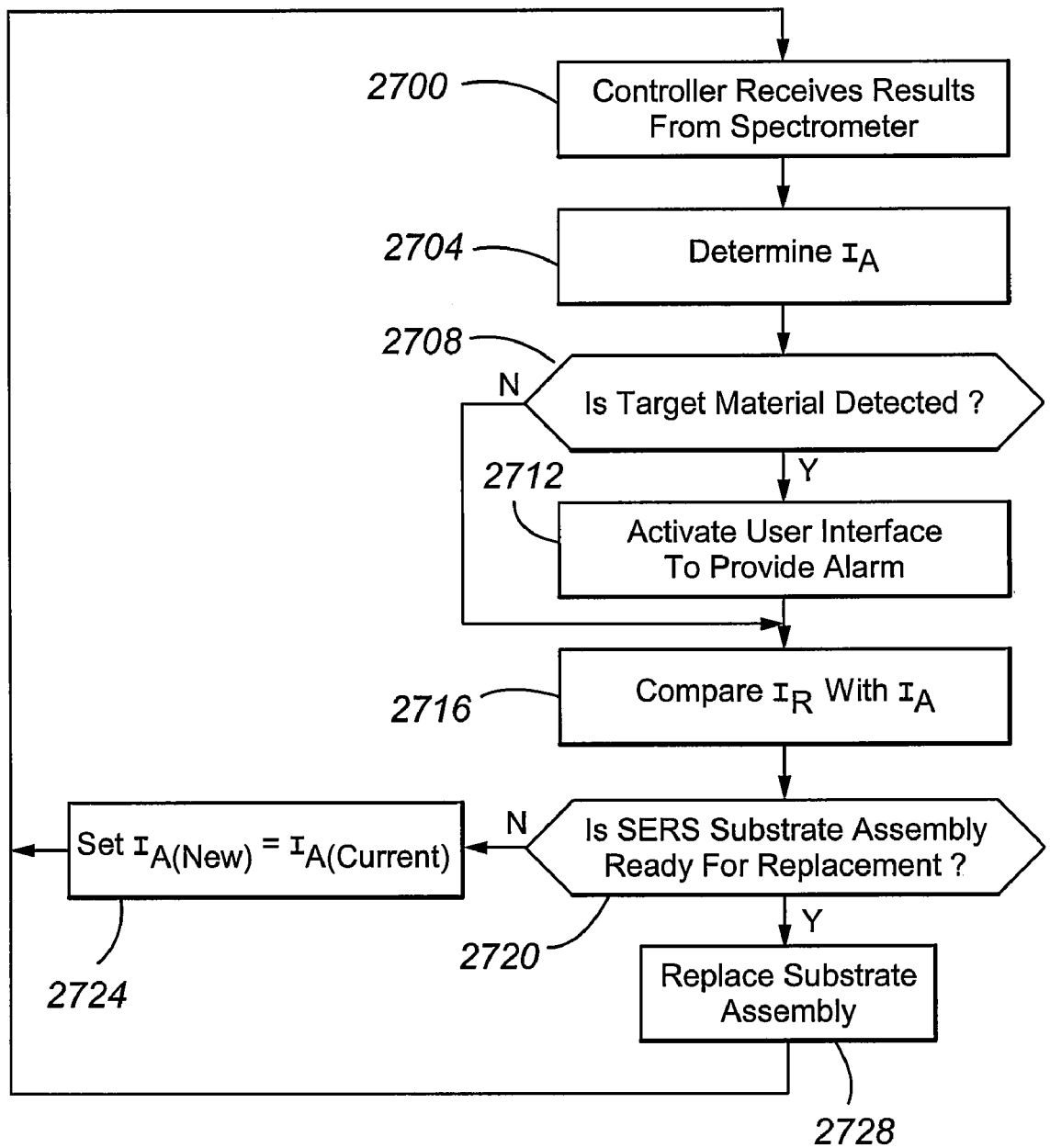
FIG. 27 is a flow chart depicting a method of operating the controller of the first embodiment.

Referring now to FIG. 27, the controller 1128, in step 2700, receives, via the cable 112, the results from the detector 1136 and obtains a time stamp for the sample from the timer 1134.

In step 2704, the controller 1128 determines $I_A$ by known techniques. In one configuration, $I_A$ is provided by the detector. As will be appreciated, $I_R$ is the Raman signal from the substrate assembly prior to sample measurements being performed while $I_A$ is related to the currently adsorbed analytes on the substrate assembly. Because the rate of desorption of the analytes is relatively low, $I_A$ is related to the analytes in the current sample and in all previously tested samples.

In decision diamond 2708, the controller 1128 determines whether $I_A$ indicates the presence of a target material in the currently tested sample. When the substrate assembly is not reused after a positive detection, this determination is based solely on the spectral characteristics, such as the distribution of $I_A$ peaks and magnitude of $I_A$. When the substrate assembly is reused after a positive detection, this determination is based on the difference between the previously encountered spectral characteristics, such as spectral distribution and/or magnitude of $I_{A(OLD)}$, and the currently recorded spectral characteristics, such as spectral distribution and/or magnitude of $I_{A(CURRENT)}$. When $I_A$ indicates that the target material is present in the current sample, the controller 1128, in step 2712, activates the user interface 1124 to show an alarm.

When $I_A$ indicates that the target material is not present in the current sample or after step 2712, the controller 1128 determines a ratio of $I_R$ to $I_{A(CURRENT)}$.

In decision diamond 2720, the controller 1128 determines whether the SERS substrate assembly is ready for replacement. This is determined by comparing the ratio against a selected threshold. Depending on how the ratio is computed, so long as the ratio is greater (or less) than the selected threshold the SERS substrate assembly is not ready for replacement. When the difference in magnitude is less (or greater) than or equal to the selected threshold, the SERS substrate assembly is ready for replacement. In one configuration, the SERS substrate assembly is replaced after each cycle or after each positive detection of a target material.

If the substrate assembly is ready for replacement, the substrate assembly is replaced in step 2728.

If the substrate assembly is not ready for replacement, the controller 1128, in step 2724, sets the previously recorded spectral characteristics, denoted by $I_{A(OLD)}$, equal to the currently recorded spectral characteristics, denoted by $I_{A(CURRENT)}$.

After performing either of steps 2724 or 2728, the controller 1128 returns to and repeats step 2700.

Other Raman Excitation Assembly Configurations

Figure 12:
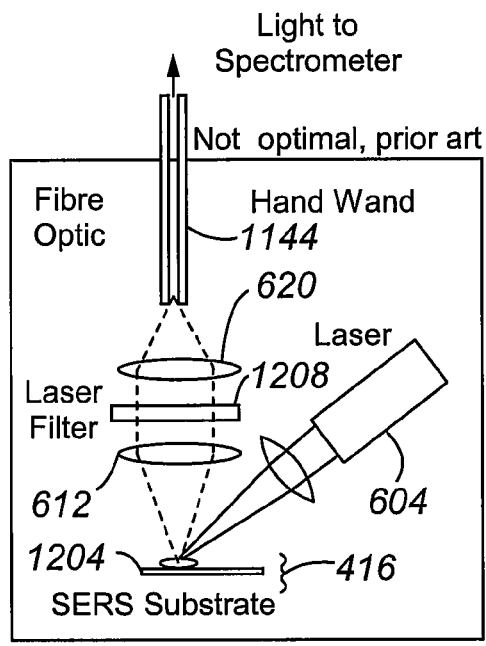
FIG. 12 depicts a cross-section of an optical system according to a first configuration.

Referring to FIG. 12, an alternate Raman excitation assembly configuration is shown. The laser 604 irradiates the SERS substrate assembly 416 from an angle relative to the SERS substrate planar surfaces 1204, other than normal. The scattered light passes through a concentrating lens 612 to form a collimated beam. The collimated beam passes through a laser filter 1208 to remove unwanted wavelengths of reflected light. The filtered beam then passes through concentrating lens 620, which focuses the filtered beam 620 onto a fiber optic 1144. This configuration may not optimal as the laser light impacts the SERS substrate assembly at a non-normal angle.

Figure 14:
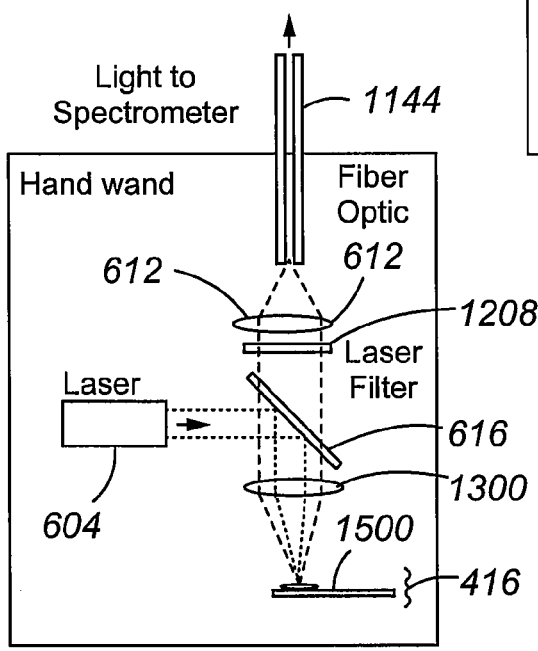
FIG. 14 depicts a cross-section of an optical system according to a third configuration.
Figure 36:
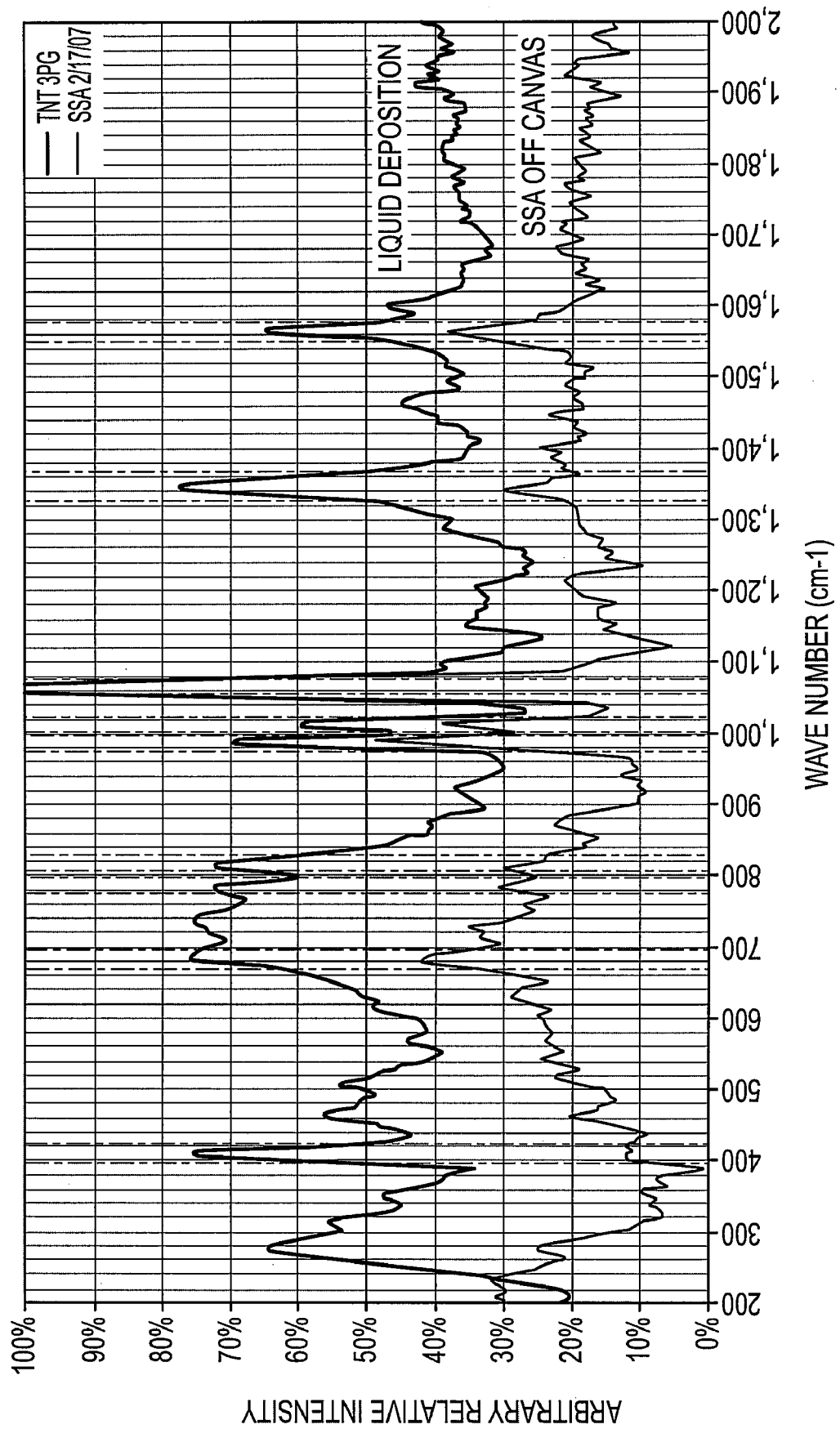
FIG. 36 is a plot of relative intensity (units) (vertical axis) against wave number ($cm^{-1}$).(horizontal axis)
Figure 37:
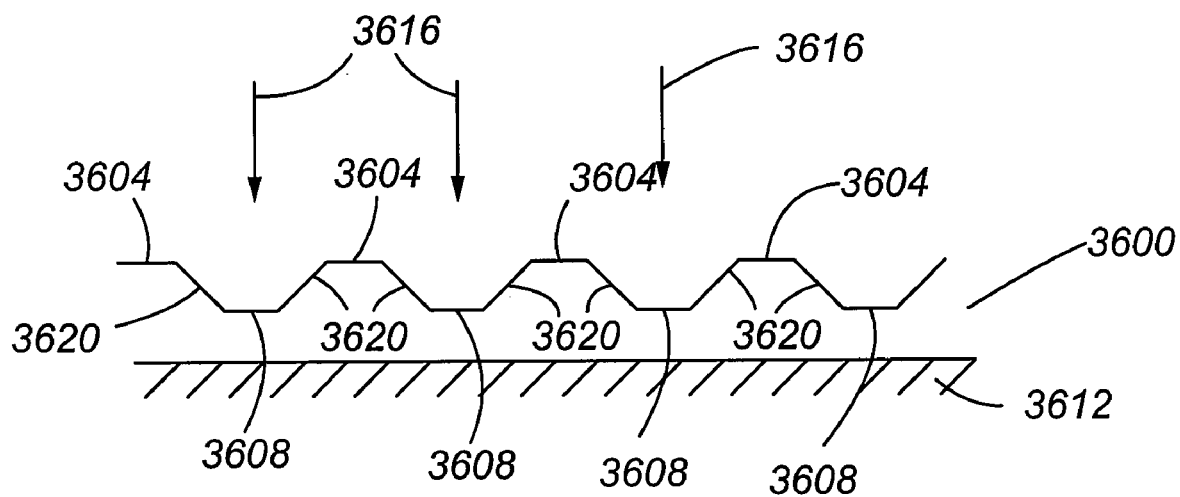
FIG. 37 is an exploded cross-sectional view of the metal layer according to a substrate configuration.
Figure 38:
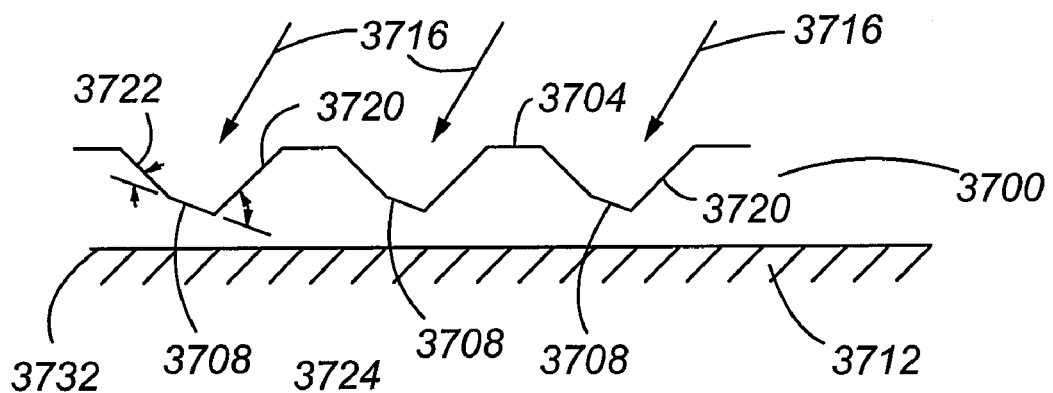
FIG. 38 is an exploded cross-sectional view of the metal layer according to another substrate configuration.

As shown in FIGS. 37-38, a substrate that has a tailored nanometer scale surface patterning may make non-normal irradiation optimal and obviate the need for beam splitter 616 in FIG. 14, further simplifying the optics. FIG. 36 shows the textured metal layer 3600 of the substrate assembly according to a conventional design. The layer 3600 has a plurality of peaks 3604 and valleys 3608 resulting, in part, from the nano-texturing of the underlying substrate 3612. The peaks and valleys require, for optimal spectral results, the laser radiation 3616 to be normal to the surface, or plane of the substrate 3612, as shown. In contrast, FIG. 37 shows the textured metal layer 3700 of the substrate assembly according to an unconventional design. The layer 3700 has a plurality of peaks 3704 and valleys 3708 resulting, in part, from the nano-texturing of the underlying substrate 3712. The shoulders 3720 and 3722 of the peaks and valleys are asymmetrical such that the angle 3724 of one shoulder 3720 is significantly less than the angle 3728 of the opposing shoulder 3722. The valley floor 3708 is substantially orthogonal to the incoming radiation 3716 and optical path axis of the radiation. The relationship of the incident angles of the shoulders 3720 and 3722 with respect to the valley floor 3708 in FIG. 37 for non-normal irradiation is substantially identical to that with respect to the incident angles of the shoulders 3620 with respect to the valley floor 3608 in FIG. 36 for normal irradiation. However while the planes of the shoulders 3620 of FIG. 36 form substantially equal angles relative to the plane of the substrate 3612, the shoulders 3720 and 3722 of FIG. 37 form substantially unequal or different angles with the plane 3732 of the substrate 3712. The asymmetrical peaks and valleys are typically formed by tailoring the nano-texturing to permit the use of a desired optical path orientation relative to the substrate. The optical path orientation is non-normal to the underlying plane 3732 of the substrate 3712.

Figure 13:
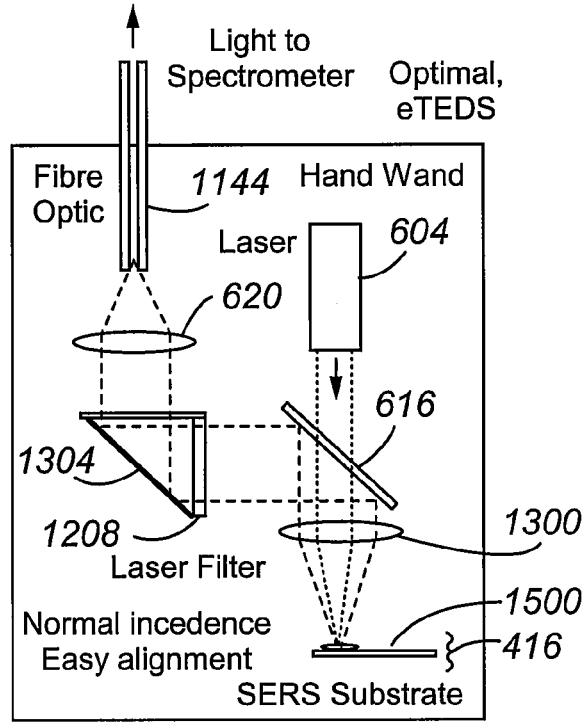
FIG. 13 depicts a cross-section of an optical system according to a second configuration.

Referring to FIG. 13, another Raman excitation assembly configuration is shown. The laser 604 provides a radiation beam directed toward beam splitter 616, which reflects substantially all of the beam. The beam then passes through a concentrating lens 1300, which focuses the beam onto the active area of the SERS substrate assembly 416. Scattered light passes back through the concentrating lens 1300 which converts the divergent light into a collimated beam. The collimated beam impacts the beam splitter, which directs substantially all of the beam towards optical filter 1208. The filtered beam passes through a prism 1304, which redirects the light to the concentrating lens 620. The concentrating lens 620 focuses the redirected beam onto the fiber optic 1144. The angle of the optical path 1508 relative to the various planes 1500 of the SERS substrate assembly typically ranges from about 80 to about 90 degrees and more typically is about 90 degrees.

Referring to FIG. 14, yet another Raman excitation assembly configuration is shown. This configuration is similar to that used in the system 100. The laser 604 provides a radiation beam that contacts a beam splitter 616, which directs substantially all of the beam towards the concentrating lens 1300. The concentrating lens concentrates the beam onto the active area of the SERS substrate assembly 416. Scattered light passes through beam splitter 616, which passes substantially all of the scattered light. The scattered light then passes through the optical filter 1208, and the filtered light through the concentrating lens 620. The concentrating lens 620 focuses the redirected beam onto the fiber optic 1144.

Figure 16:
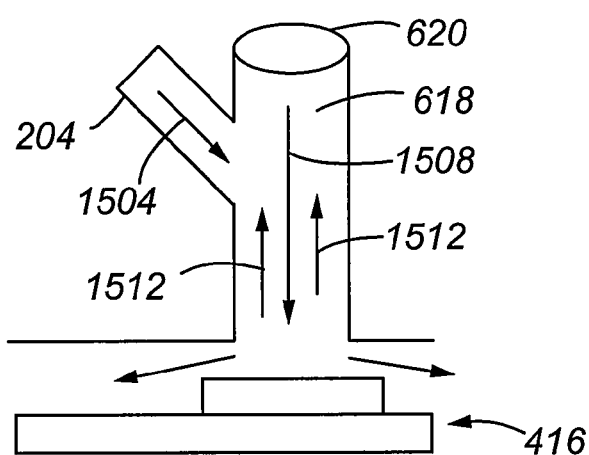
FIG. 16 depicts a cross-section of an optical system according to a fifth configuration.

Referring to FIG. 16, yet another Raman excitation assembly configuration is shown. The difference between the configurations of FIGS. 15 and 16 is that the inlet 204 of the configuration of FIG. 15 intersects the beam path 618 in close proximity to the substrate assembly 416 so that most of the sample 1504 contacts the substrate assembly 416 at a non-normal angle of flow relative to the planes 1500 of the substrate assembly, while the inlet 204 of the configuration of FIG. 16 intersects the beam path 618 at a distance from the substrate assembly 416 so that most of the sample 1504 contacts the substrate assembly 416 at a near normal angle of flow relative to the planes 1500 of the substrate assembly. Typically, upon contact with the metal surface the angle of flow of the sample 1504 relative to the planes 1500 ranges from about 65 to about 90 degrees.

The configuration of FIG. 16 can require a longer Raman focal length to get a columnar gas flow or have a lot of turbulence in the sample gas flow before engaging the active metal surface of the substrate assembly 416. However, directing the (gas) sample 1504 flow normal to the SERS substrate surface can enhance the interaction of heavier analytes with the metal surface. Heavier gas molecules will have more momentum and, in turn, a greater probability of impacting the metal surface when the sample carrying conduit ends abruptly, just above the surface of the substrate assembly. The molecular beam effect applies as long as the directed gas flow has a velocity component that is normal to the SERS substrate surface; thus, it applies, though not as strongly, when the gas flow is at an angle of 45° to the surface as shown in FIG. 15. The turbulence can adversely impact the ability of lighter gas molecules to impact with the metal surface of the SERS substrate assembly.

Other Embodiments

Figure 17:
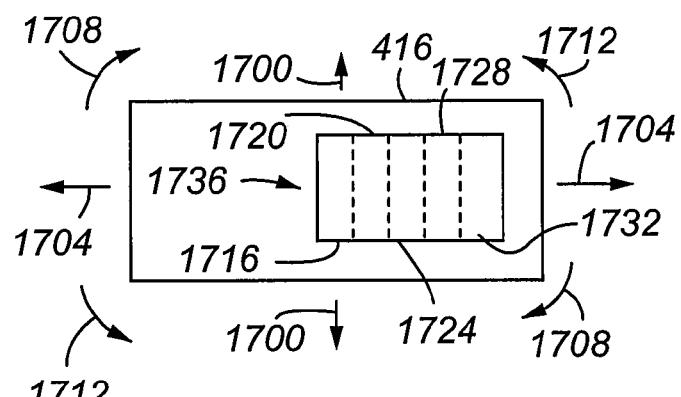
FIG. 17 depicts a cross-section of a movable SERS substrate according to a second embodiment.

Referring to FIG. 17, another embodiment will be discussed. In this embodiment, movement of the substrate assembly in any or all of the directions 1700, 1704, 1708, and 1712 allows sequential or co-integrated measurement over spatially separated substrate features 1716, 1720, 1724, 1728, and 1732 that have unique features, such as different coatings, reference signals and/or other physical variations. Different coatings applied in each feature zone can increase the sensitivity and specificity of the SERS instrument for target chemical analyses over multiple types of target materials. By way of example, each feature 1716, 1720, 1724, 1728, and 1732 can be configured to adsorb different target chemical compounds. This can be done by applying, in each feature zone, different thiols having different active groups in each feature zone. In this manner, a sample having multiple different target materials may be analyzed, for all analytes, using a common SERS substrate assembly. Each zone has its own spectral results, which are compared against a respective $I_R$ signal to identify occurrences of the corresponding target material.

Signal acquisition from tailored SERS substrate coatings can be increased by serially moving the active area 1736 of the substrate assembly into the Rama laser focus (for serial data) or dynamically moving and/or spinning, the substrate during a single acquisition for combined integrated data (for multiplex data). Using nano-fabrication techniques, coating intercalation can be performed on the nano scale, thus allowing multiplex data to be acquired with a single laser beam with a focus on the order of tens to hundreds of micrometers in diameter.

While FIG. 17 is discussed with reference to moving the SERS substrate assembly during irradiation, it is to be understood that the optical path of the incoming radiation may also or alternatively be moved relative to the SERS substrate assembly.

Figure 18:
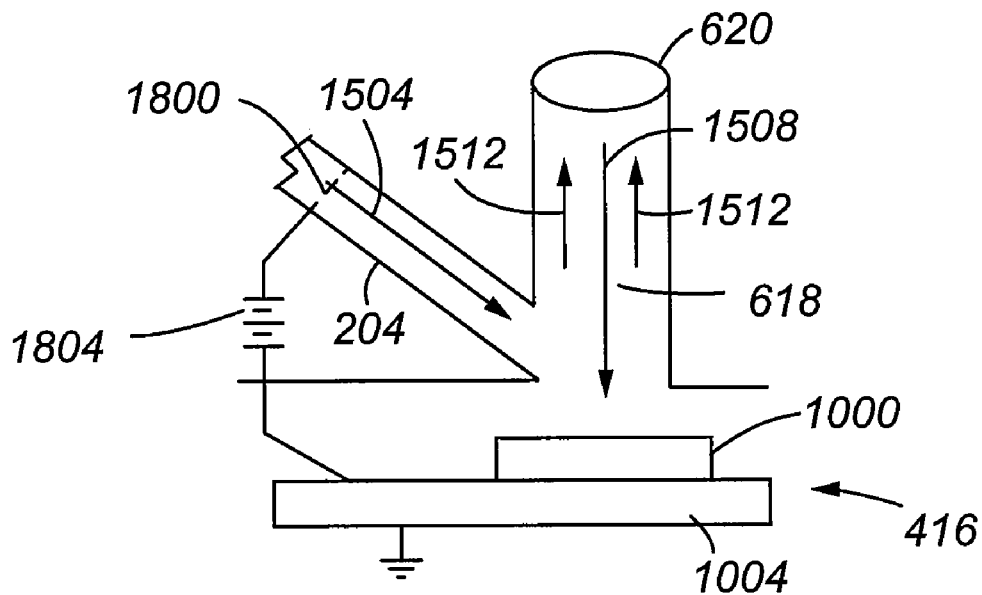
FIG. 18 depicts a cross-section of an optical system according to a third embodiment.

FIG. 18 depicts yet another embodiment in which target material condensation is effected or facilitated using electrostatic or electrodynamic techniques. Ion mobility spectrometers, IMS, charge the analyte to perform their measurement and detection of the trace chemicals. While SERS is an optical technique and does not require a charge to be imparted on the analyte, the SERS substrate is electrically conductive. If the sample, in gas form, flowing towards and across the SERS substrate surface was electrically charged by one or more electrodes 1804 positioned in the inlet 204, and the supporting substrate 1004 was maintained at ground, or at an opposite potential to the electrode 1800, the attractive force between the target material or analyte and the SERS substrate assembly surface could be increased substantially, and the analyte readily concentrated at levels beyond what normal turbulence and Brownian motion would achieve. This application of electrostatic, or even dynamic, electrical fields can increase the sensitivity of SERS analyses for analytes in a gas flow. Preferably, the interlock described above with reference to access door access would also interrupt the supply of power by the power source 1804 (which is typically the same as power source 1132) upon user access to the SERS substrate.

Figure 20:
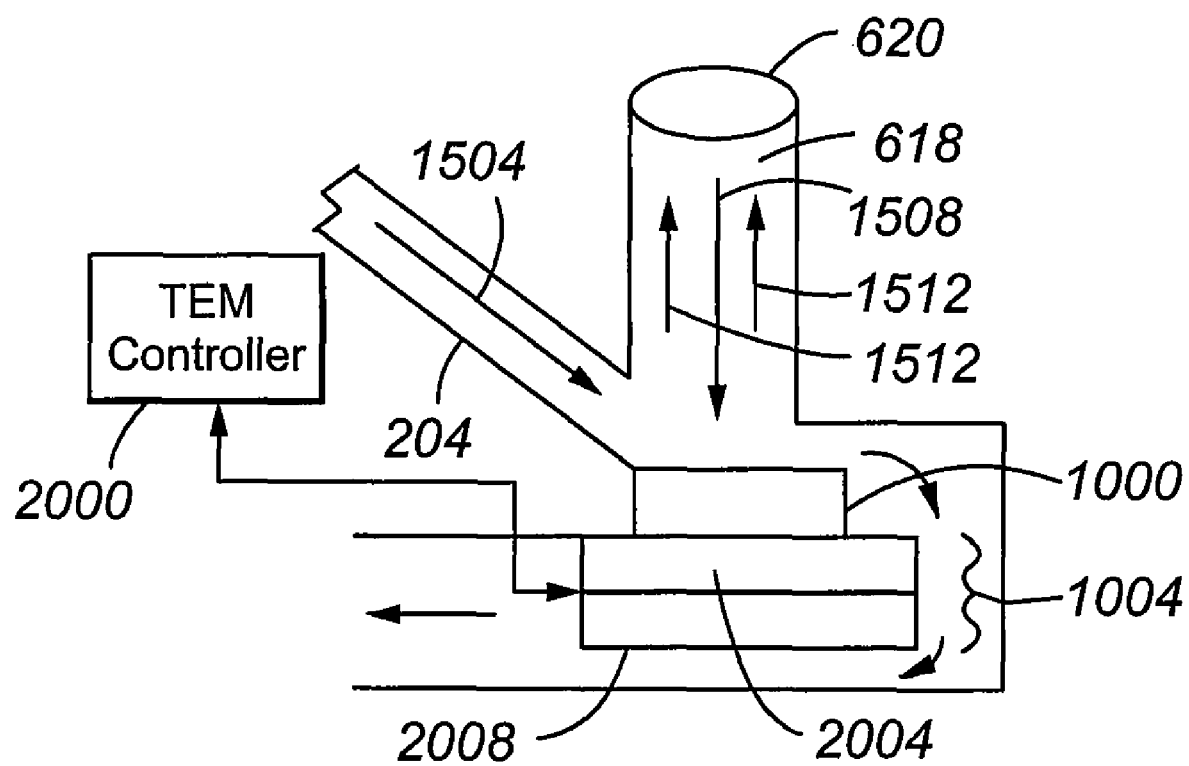
FIG. 20 depicts a thermal-electric optical system according to a fourth embodiment.

FIG. 20 depicts a system configuration according to yet another embodiment. Low vapor pressure, high boiling point, analytes liberated from surfaces using SSA are encouraged to adsorb onto the SERS surface by cooling (or heating) the active metal surface to a temperature below (or above) the ambient temperature. This is accomplished in one configuration using a thermal-electric (TEM) controller 2000. The TEM controller controls the application and polarity of voltage applied across first and second portions 2004 and 2008 of the carrying substrate 1004. As will be appreciated, the thermal-electric effect occurs when a voltage is applied across a semiconductor junction. One side of the junction is heat rejecting and the other heat absorbing. In a first operating mode, the first portion 2004 has a first polarity and acts as a heat absorber and in a second operating mode a second different polarity and acts as a heat rejector, while the second portion 2008 in the first operating mode has the second polarity and acts as a heat rejector and in the second operating mode has the first polarity and acts as a heat absorber. The controller 2000 can select between the first and second operating modes depending on the target material to be detected and/or interferents. In the first operating mode, the active metal surface is cooled to encourage condensation and adsorption of a selected analyte while in the second operating mode it is heated to discourage condensation and adsorption of a selected specific lower boiling point analyte to improve the sensitivity to the high boiling point analytes. The second operating mode can also be used to elevate the SERS substrate substantially to aid in renewing the surface for improved sensitivity in a later sample collection/test cycle or at the end of an operating day when the system is idle or recharging the power supply (batteries). The second operating mode is typically not attractive for a low-power, handheld instrument in operation, but could readily be exploited in an application where the apparatus is used in a stationary system for trace chemical monitoring. The carrying substrate, in the embodiment of FIG. 20, is itself configured as a thermal-electric, Peltier, device. In other embodiments, the carrying substrate is mounted on a separate thermal-electric Peltier device. In reference to FIG. 20 the sample flow 1504 is directed across the second portion 2008 of the carrying substrate removing excess heat from the carrying substrate without requiring a separate means to direct heat exchange to the second portion.

Another target material detection system embodiment will now be described with reference to FIGS. 21A-C. In this embodiment, SSA is used to liberate collected materials on a surface (filter or solid) in real time without having to thermally ramp a substrate (stainless steel filter) and reset the filter temperature for a subsequent acquisition. The system 2100 includes first and second valves 2104 and 2108, each serving two possible paths. The first valve 2104 has a first outlet along a first path 2112 and a second outlet along a second path 2116, while the second valve 2108 has a first inlet along the second path 2116 and a second inlet along the first path 2112. The system further includes a filter 2120 for sample collection, a strobe light 2124 for target material mobilization, a preferably high-speed target material sensor 2128 for detecting a target material, a third valve 2132 connected to an air filter 2136 for drawing in ambient air, and an air pump 2140. A plurality of filters 2120 can be on a dispenser, such as a roll, which is advanced one filter at-a-time prior to the commencement of each sample collection and measurement cycle. Each filter 2120 can also be time stamped by a printer or otherwise have or be given a unique identifier so that the filter 2120 can be matched with the sampled object. This can be important for law enforcement or immigration applications where evidence is to be collected.

In a first operating mode, a sample 2144 is received from a part of an animate or an inanimate object and passed along the first path 2112 through the filter 2120. In the first operating mode, the second path 2116 is shut off and isolated by the first and second valves, the strobe and sensor are inactive, and the third valve 2132 is closed. As the sample passes through the filter 2120, which may be a polymeric material, paper, metal, and the like, various substances, potentially including target materials, are deposited on the filter.

After a predetermined time, the system 2100 enters into a second operating mode. In the second operating mode, the first and second valves are closed to isolate the first path 2112 but open to pass the sample along the second path 2116 and through the pump 2140. A negative air pressure is present along the first path 2112 as generated by the operation of target material sensor 2128. The third valve 2132 is open, thereby drawing air through the air filter 2136 into the first path 2112 and through the filter 2120. While in the second operating mode, the strobe 2124 is activated for one or more periods to mobilize the substances on the filter 2120. The air will entrain the substances and, in response to the negative pressure, carry them into the sensor 2128. The sensor 2128 is activated to detect any target materials in the substances entrained in the air.

Prior to re-entry into the first operating mode, a new filter 2120 is positioned in the first path 2112 to receive a next sample from the same or another object.

This embodiment can apply SSA with a high speed detector to assess for trace chemicals in large volumes of sampled air. In one application, high volume air sampling is performed at a security portal through which people or luggage pass. As the person or luggage passes through the portal, it is subjected to a flow of air. SSA can very rapidly desorb analytes collected on the filter 2120 that large volumes of air have passed through.

These advantages are apparent when compared to conventional security portal sampling systems. In current sampling systems employed in airport security portals, the sampled air is passed through an electrically conducting stainless steel filter. After collection of dust and adsorbed chemicals, the screen (filter) is heated by passing a high current at a low voltage through the conductive filter. This liberates adsorbed materials through vaporization. The liberated vapor is then sampled typically with an IMS instrument. Before evaluation of a second air sample, the filter must be cooled to ambient temperatures. The duty cycle of conventional trace explosive portals is illustrated in the top diagram of FIG. 21C. In first and second sampling periods 2100a,b, first and second samples are collected using high flow air from first and second surfaces or objects. After the first sampling period 2100a, the filter is electrically heated during a desorption period 2104, and the desorbed sample analyzed by the IMS instrument during a detection period 2108. The detection period 2108 includes not only a time interval to analyze the sample but also to reset the concentrator and cool the filter (which cooling is performed in parallel with the detection sequence) for the next sample. The entire sequence of the conventional portal system takes between about 30 and 60 seconds per sample. The conventional portals have had, in operation, a high rate of false positives and, as a result, are not considered reliable and a minor tool in security screening today.

In contrast, the cycle timing diagram for the embodiment of FIGS. 21A-B is depicted in the lower diagram of FIG. 21C. With the SSA enabled technique the filter medium need not be stainless steel or electrically conductive. In the time period required for the first and second sampling periods 2100a,b, a series of first, second, third, fourth, and fifth sampling periods 2112a-e are performed, respectively, on first, second, third, fourth, and fifth surfaces or objects. Between each pair of adjacent sampling periods, a corresponding SSA and detection cycle 2116a-e and 2120a-e is performed. The much more rapid sampling, SSA and detection cycles provide, for the first surface or object, a target time savings time interval 2124.

As can be seen from FIG. 21C, the SSA event is much faster and liberates not only vapor but also particles, further increasing the vapor liberation for subsequent analysis. The conventional system requires the high volume air sample to be started and stopped during liberation and analysis. Using SSA, the high volume air sampling need not be stopped but only bypassed for a matter of about 1 to 5 seconds before taking the next sample. The total analysis time can be shortened by up to about 20 seconds by not having to thermally heat the collected sample and then cool the screen for subsequent use. Additionally, the detection time will be greatly shortened by the use of SERS. The use of SSA will allow the system to operate at much higher throughput. The system of FIGS. 21A-B also need not discretely activate and stop the high flow sampling system. The high flow can be maintained and the samples collected to correspond with an event. After the event, particularly the screening of a person or other object, the high flow is bypassed along path 2116, as shown in FIG. 21B, briefly as the SSA is activated to take a sample and perform the chemical analysis.

If the filter 2102 is a renewed media between samples the filter may be fabricated with detectable material, a reference material, that improves sensor performance. The reference material is a material having a similar, but different, spectral response to the target material of interest. To avoid false positives, the reference material preferably produces a spectral peak in the scattered radiation at a similar, but non-overlapping, wave number range to the spectral peak produced by the target material. For example, with TNT as the target material of interest the reference material can be sugar or toluene having a functional group other than one or more nitrite molecules in the 2, 4, or 6 position. On each filter, a predetermined amount of the reference material is deposited to produce, in each filter, a similarly sized airborne sample in response to stroboscopic desorption. In this manner, the spectral response for the reference material acts as a marker that the sample collection and detection system and its various components are working properly and that the filter pad has not been used previously. This represents a major throughput enhancement to the operation of the security portals and jets.

Figure 22:
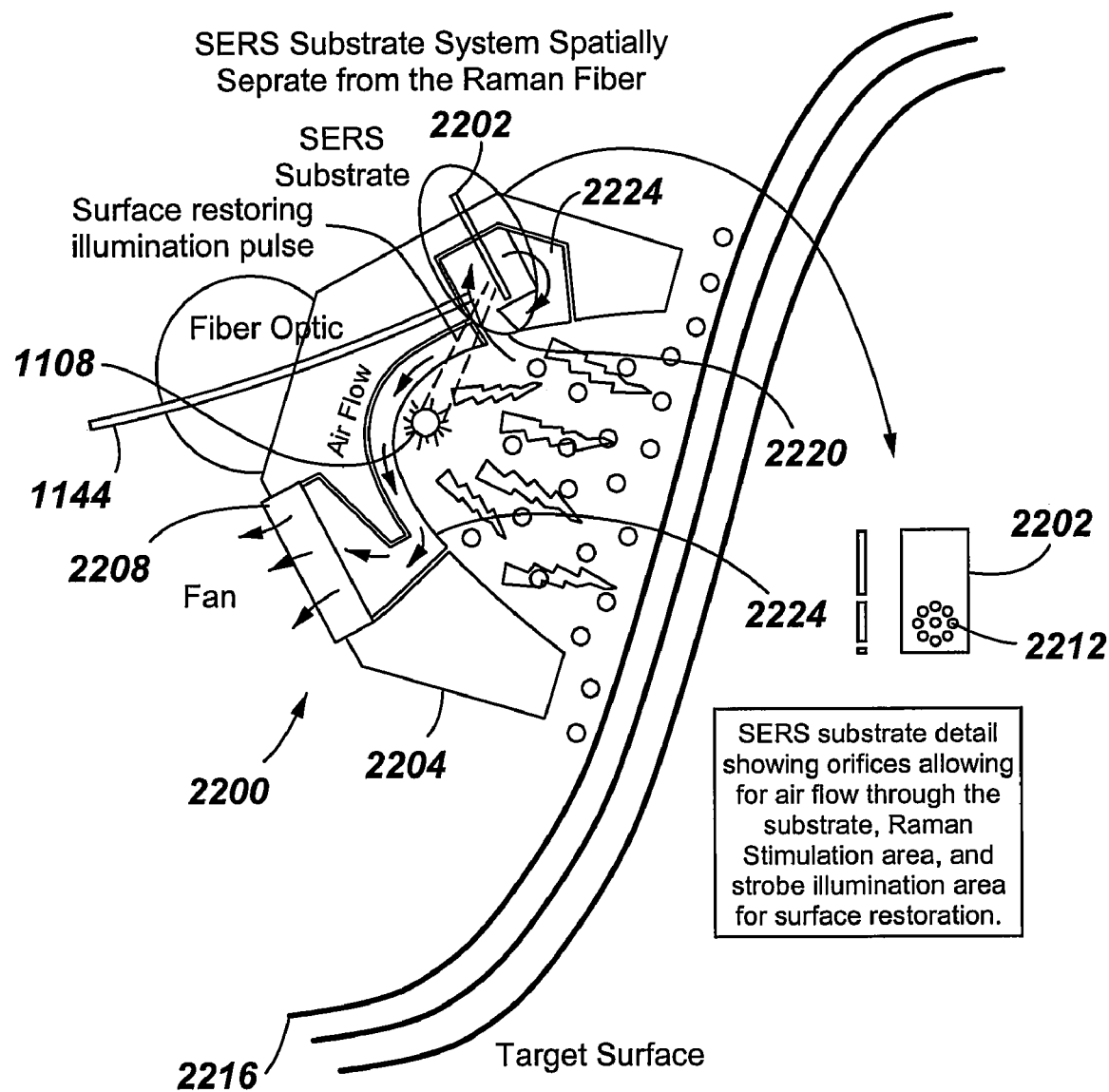
FIG. 22 is a cross-section of a detection system according to a sixth embodiment.

Another embodiment will be discussed with reference to FIG. 22. The system 2200 includes the strobe light 1108, a SERS substrate assembly 2202, fiber optic 1144, housing 2204, and fan 2208. As shown in FIG. 22, the SERS substrate assembly 2202 includes one or more orifices 2212 that allow air to flow through the substrate assembly 1120. The surface 2216 to be sampled is positioned in proximity to the housing 2200. The fan is activated to move air through the opening 2220 and substrate assembly 2202 and, as shown by arrows, along the air flow path 2224, through the fan 2208, and into the ambient atmosphere. As air passes through along the flow path 2224, the strobe light 1108 is activated to irradiate the surface 2216, thereby mobilizing any target materials located on the surface 2216. The air flow carries the entrained target materials to the substrate assembly, where it impacts the active metal surface of the substrate assembly. Laser light carried by the fiber optic 1144 contacts the active metal surface, and the scattered laser light passes along the fiber optic 1144 to the detector (not shown). This system 2200 can be used in a variety of applications, such as to test the earth for landmines, vehicles, and luggage and body parts for trace explosives and drugs.

Another system embodiment will now be discussed with reference to FIGS. 23A and B. The system 2300 is configured for liberating target materials directly from target areas, such as footwear, at a high-throughput. This system 2300 may augment and/or replace manual swipes for a high-throughput trace explosives detection system for footwear (shoes). SSA can quickly and, in a directional fashion, liberate trace chemicals, such as explosives, from footwear for rapid analysis using a suitable detector.

Figure 23A:
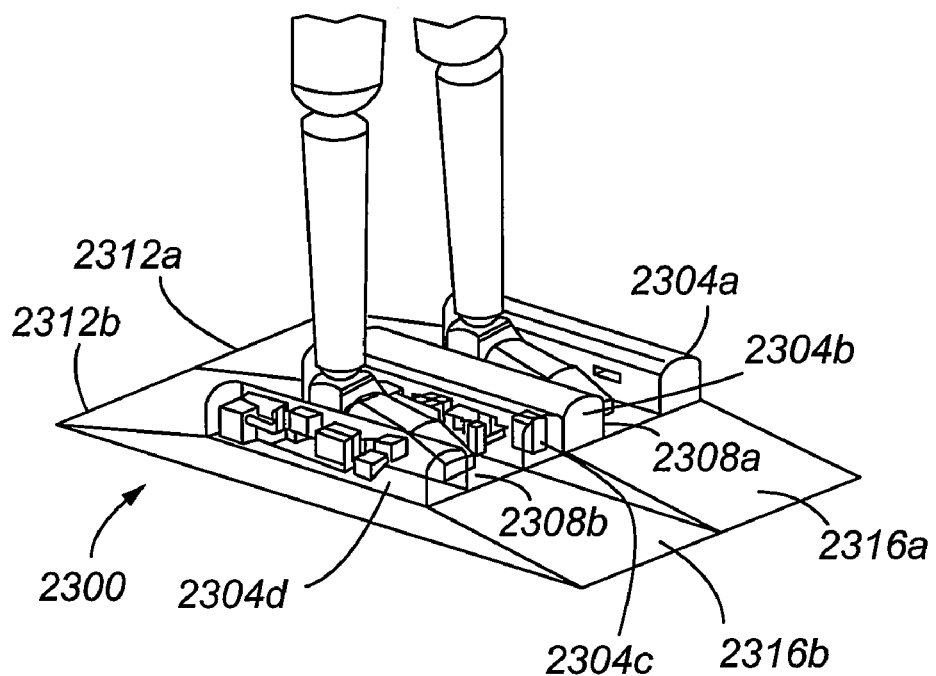
FIG. 23A is an isometric view of a detection system according to a seventh embodiment.
Figure 23B:
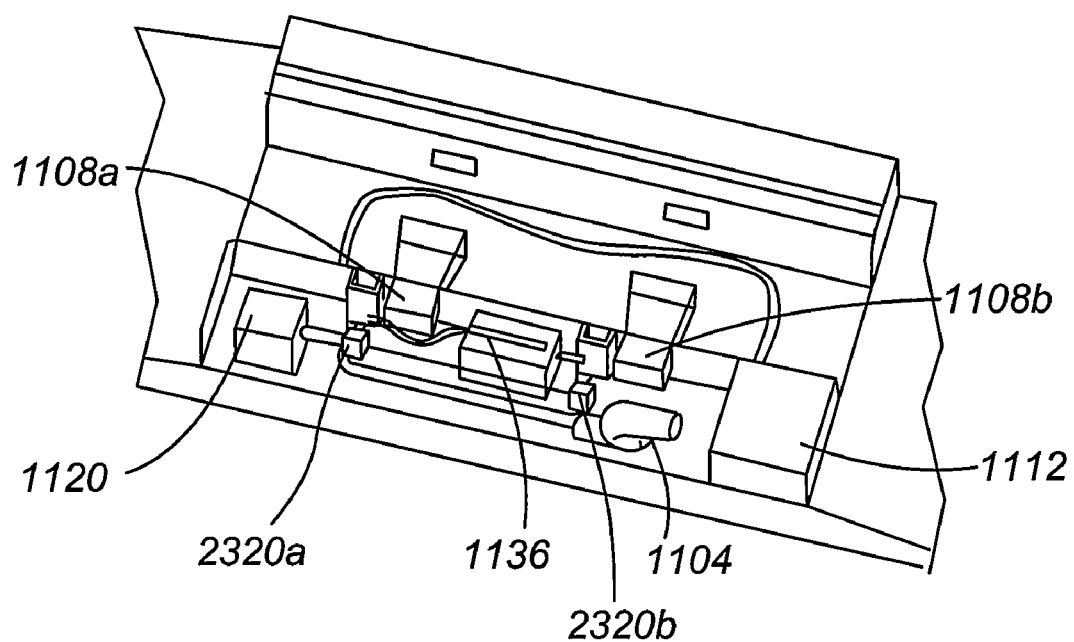
FIG. 23B depicts the detection system according to the seventh embodiment.

As illustrated in FIGS. 23A-B, the portable (or stationary) system would utilize more than one strobe light to illuminate the footwear from multiple sides and along the length. The system 2300 includes, for each foot, first and second sampling assemblies 2304*a-d*. Opposing pairs 2304*a,b* and 2304*c,d* of assemblies are separated by respective foot sampling plates 2308*a,b*, and the plates 2308*a,b* positioned between first and second ramps 2312*a,b* and 2316*a,b*, respectively. As can be seen in FIG. 23B, each sampling assembly includes first and second strobe lights 1108*a,b*, strobe electronics 1112, a detector 1136, Raman excitation assembly 1120, and air pump 1104. Adjacent to each strobe light 1108*a,b* is one or more air inputs to supply a corresponding sample to a corresponding chamber 2320*a,b* containing the SERS substrate assemblies (not shown).

The Department of Homeland Security or TSA has a requirement to check aircraft passengers' shoes for explosives. Currently, passengers are required to remove shoes as they are screened through the airport security portals. This approach is inefficient, uses an ineffective technology for screening shoes and is a major inconvenience to the passengers. The system 2300 can provide a more effective and less-intrusive explosive detection technology. The passenger shoe detection system 2300 is an automated non-intrusive technology with femtogram sensitivity and a sample time of 5 seconds providing substantially continuous throughput capability.

Figure 24A:
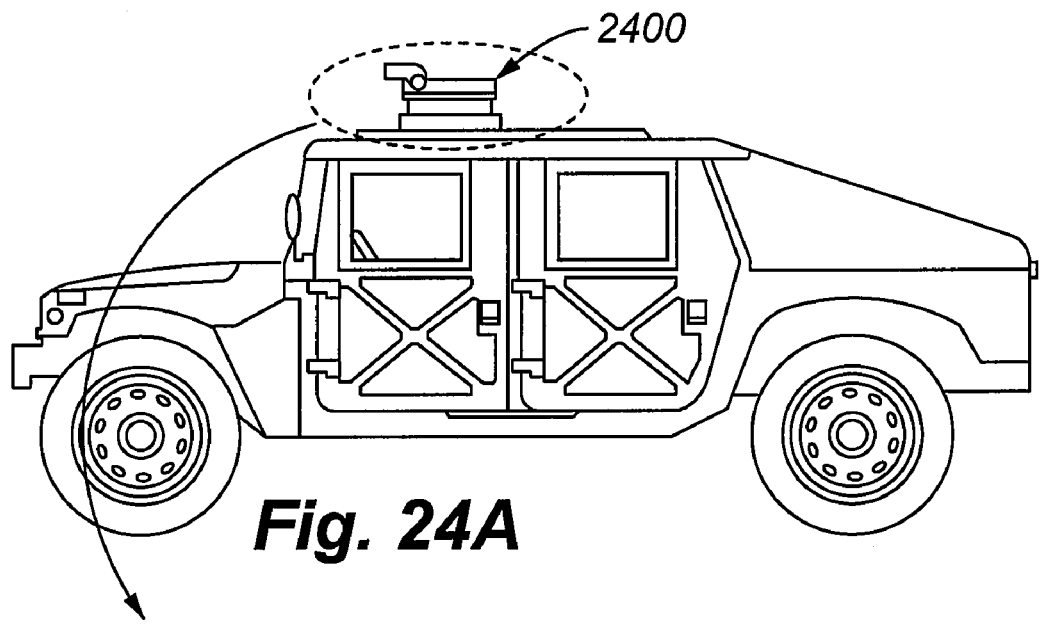
FIG. 24A depicts a vehicular detection system according to an eighth embodiment.
Figure 24B:
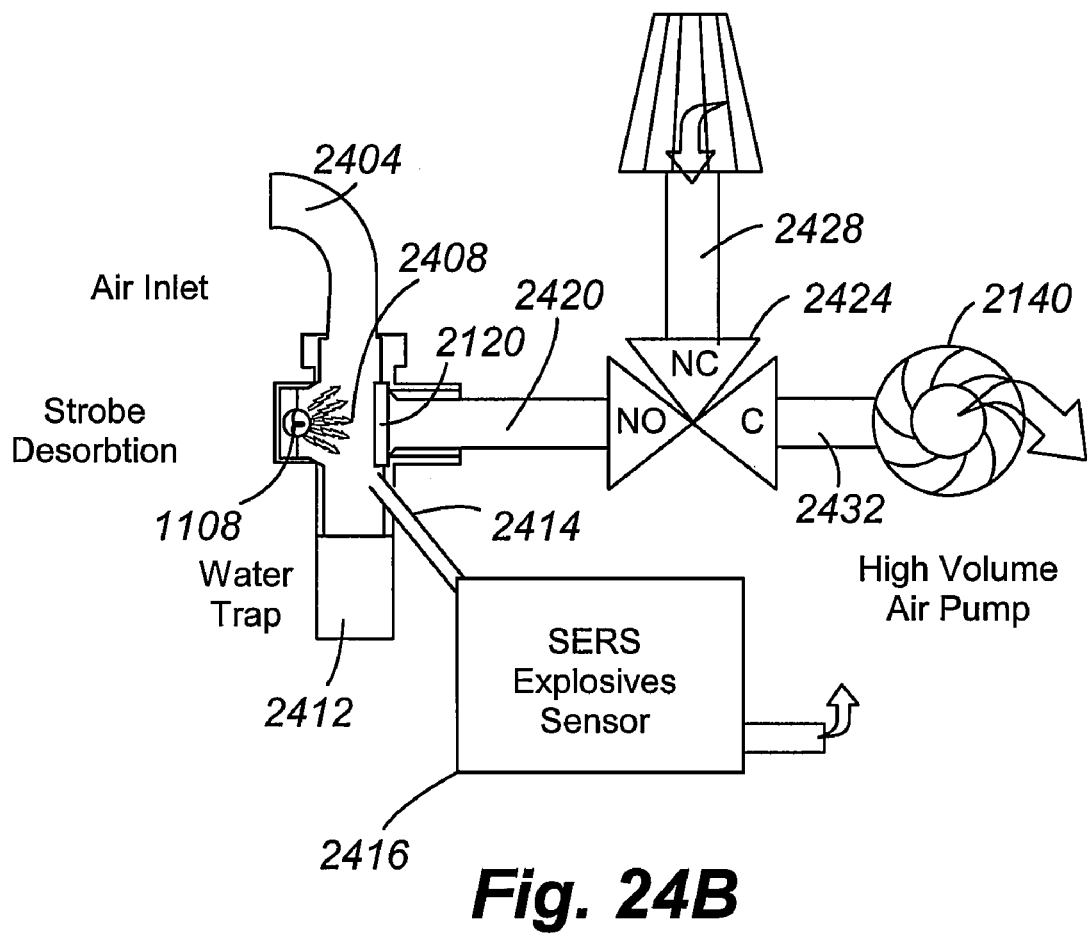
FIG. 24B depicts the detection system of the eighth embodiment.

Yet another system embodiment will be described with reference to FIGS. 24A-B. The system 2400 can be vehicle-mounted and detect airborne target materials. The system 2400 includes an air inlet 2404 to receive the sample, a strobe light 1108, an SSA chamber 2408, a water trap 2412, a filter 2120, a first flow path 2414 to a sensor 2416, a second flow path 2420, a three-way valve 2424 in communication with third and fourth flow paths 2428 and 2432, and a pump 2140. In a sample collection mode, the valve 2424 is configured to isolate the third flow path 2428 such that the air sample is drawn into the air inlet 2404, flows past filter 2120, along the second flow path 2420, through the valve 2424, along the fourth flow path 2432, and through the pump 2140, and into the ambient atmosphere. While flowing past the filter 2120, any target materials in the air flow will be deposited on the filter. In a sample detection mode, the valve 2424 is configured to isolate the second flow path 2420 while allowing air to be drawn through air filter 2136 and along the third and fourth flow paths 2428 and 2432, while the sensor draws air though the air inlet 2404 into the chamber 2408 and past the filter 2120. The air then flows along the first flow path 2414 into the sensor 2416. The strobe light 1108 is activated to mobilize and entrain any target materials on the filter 2120, which are carried into the sensor 2416 along the first flow path 2414.

EXPERIMENTAL

Figure 25:
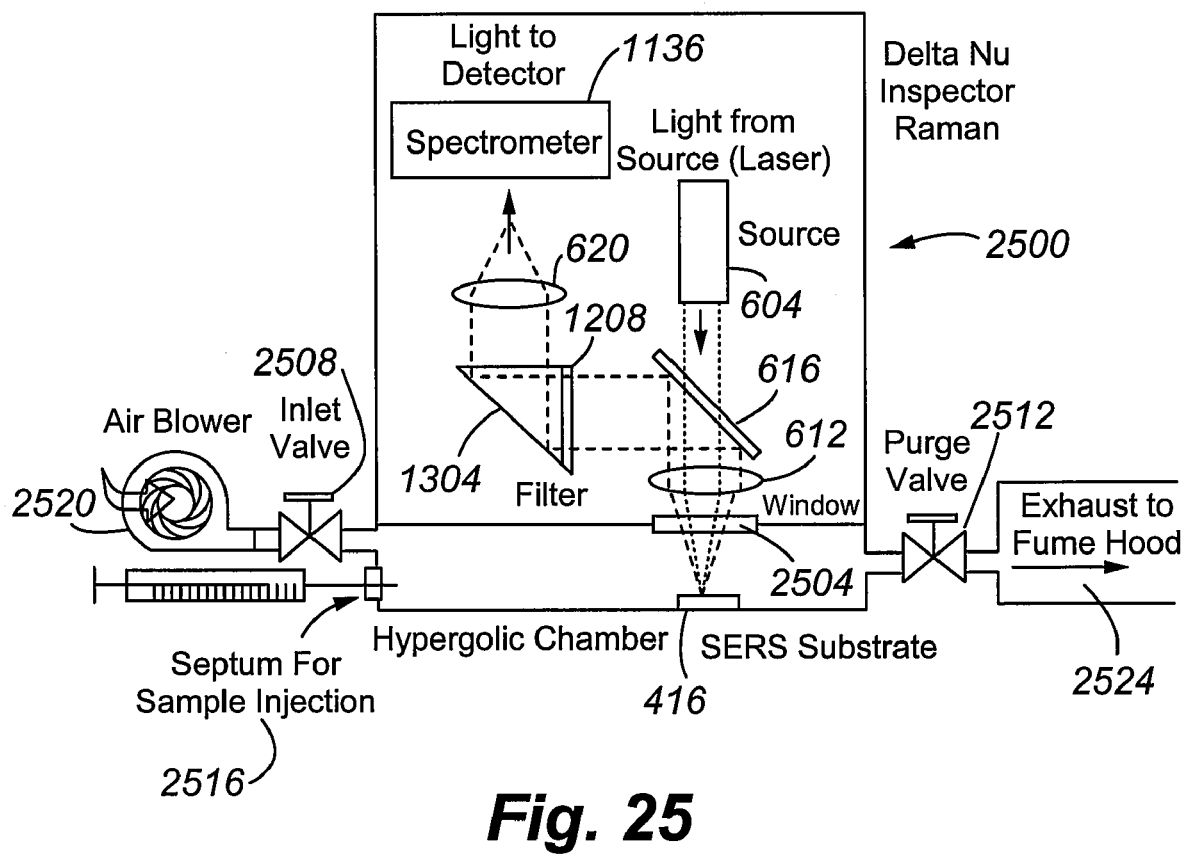
FIG. 25 depicts an experimental apparatus for testing a material detection system.

FIG. 25 depicts an experimental apparatus according to an embodiment. The apparatus 2500 includes a laser source 604, beam splitter 616, convergent lenses 612 and 620, prism 1304, optical filter 1208, detector 1136, SERS substrate assembly 416, optically transmissive window 2504, inlet and purge valves 2508 and 2512, septum for sample 2516, air blower 2520, and exhaust to fume hood 2524.

Figure 28A:
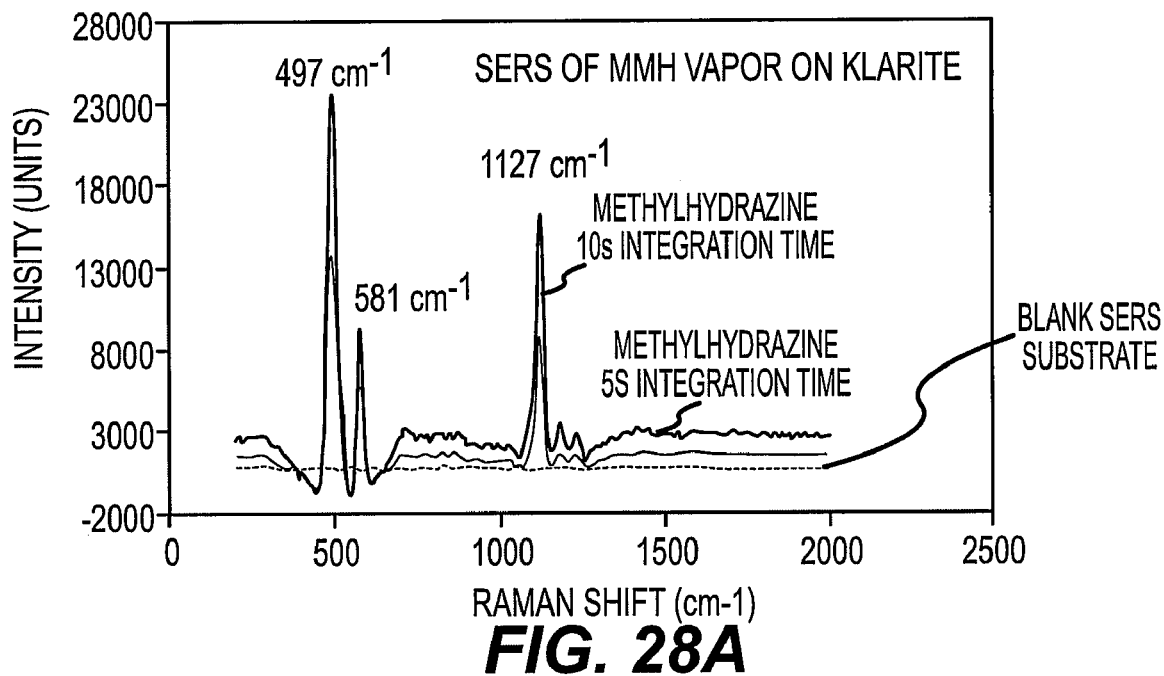
FIG. 28A is a plot of intensity (units) (vertical axis) against Raman shift ($cm^{-1}$).(horizontal axis)
Figure 28B:
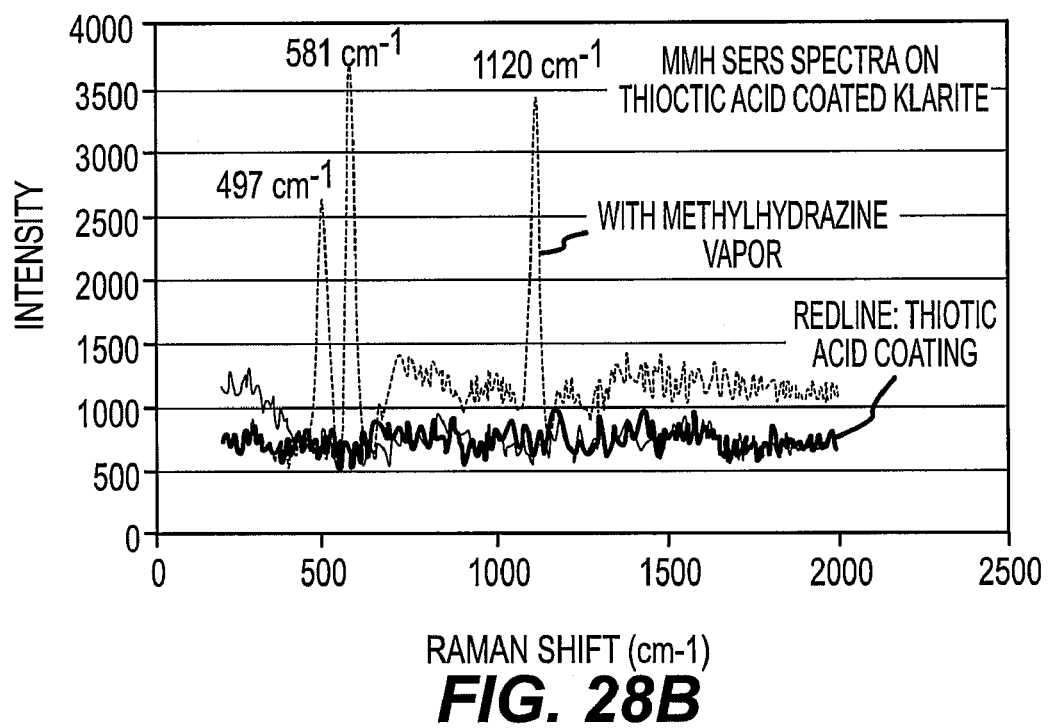
FIG. 28B is a plot of intensity (units) (vertical axis) against Raman shift ($cm^{-1}$).(horizontal axis)

FIGS. 28A and B depict SERS spectra of monomethylhydrazine or MMH collected using a Klarite substrate (FIG. 28A) and thioctic acid SAM-coated Klarite substrate (FIG. 28B). The spectrometer employed was a DeltaNu Raman spectrometer. The vertical axis is intensity and the horizontal axis is Raman shift. The peaks correspond to detected instances of MMH.

Figure 29:
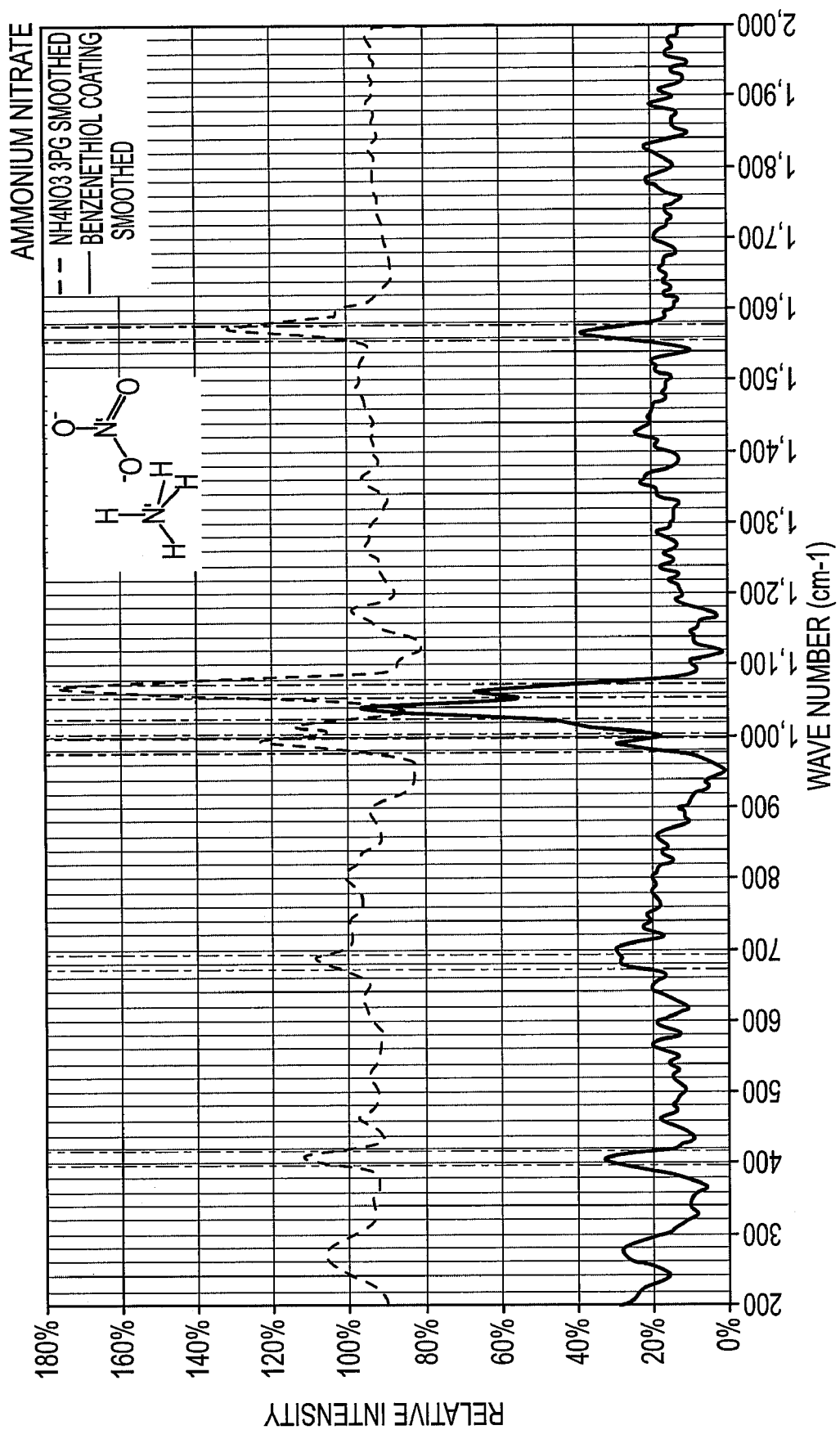
FIG. 29 is a plot of relative intensity (units) (vertical axis) against wave number ($cm^{-1}$).(horizontal axis)
Figure 30:
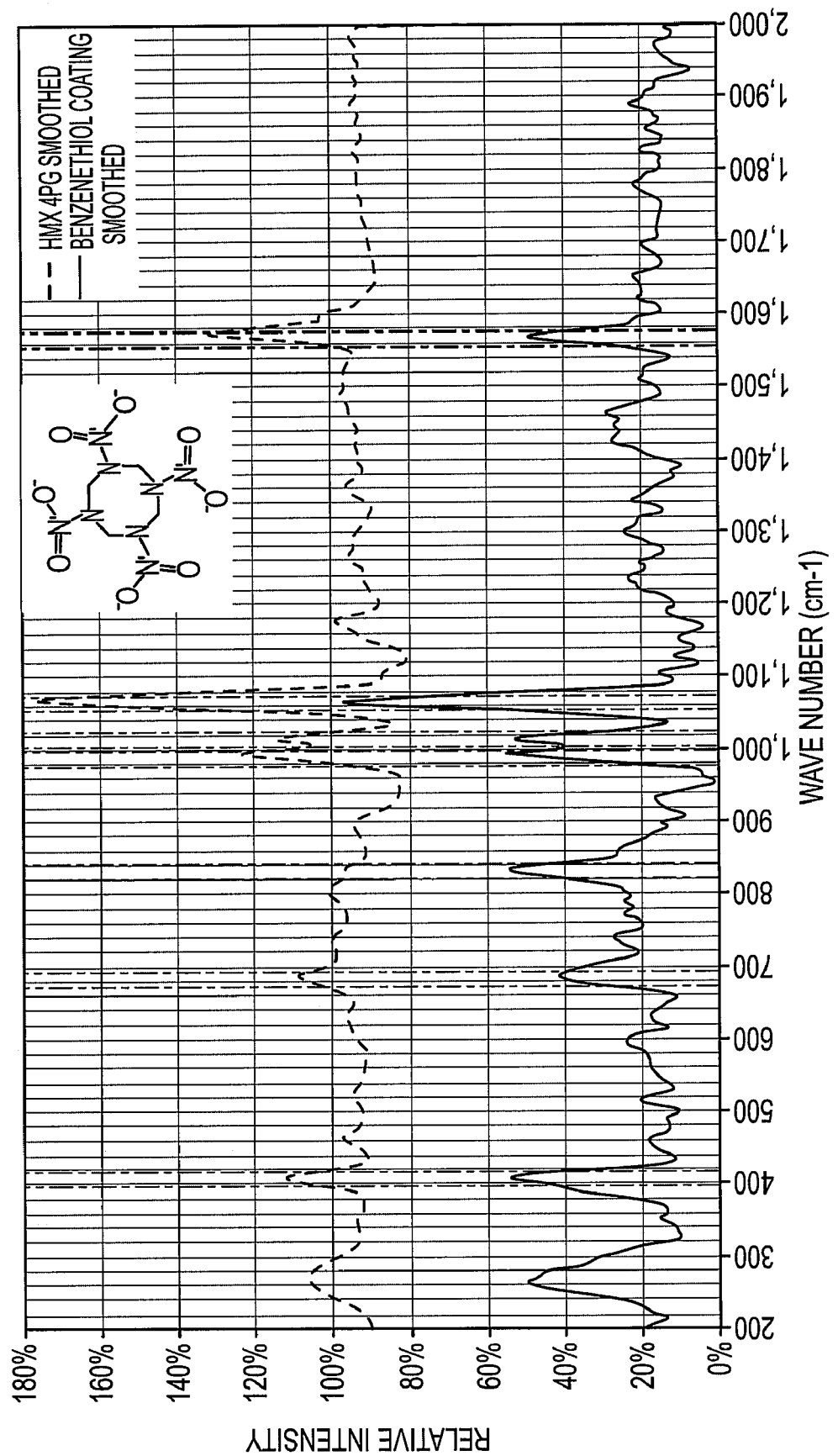
FIG. 30 is a plot of relative intensity (units) (vertical axis) against wave number ($cm^{-1}$).(horizontal axis)
Figure 31:
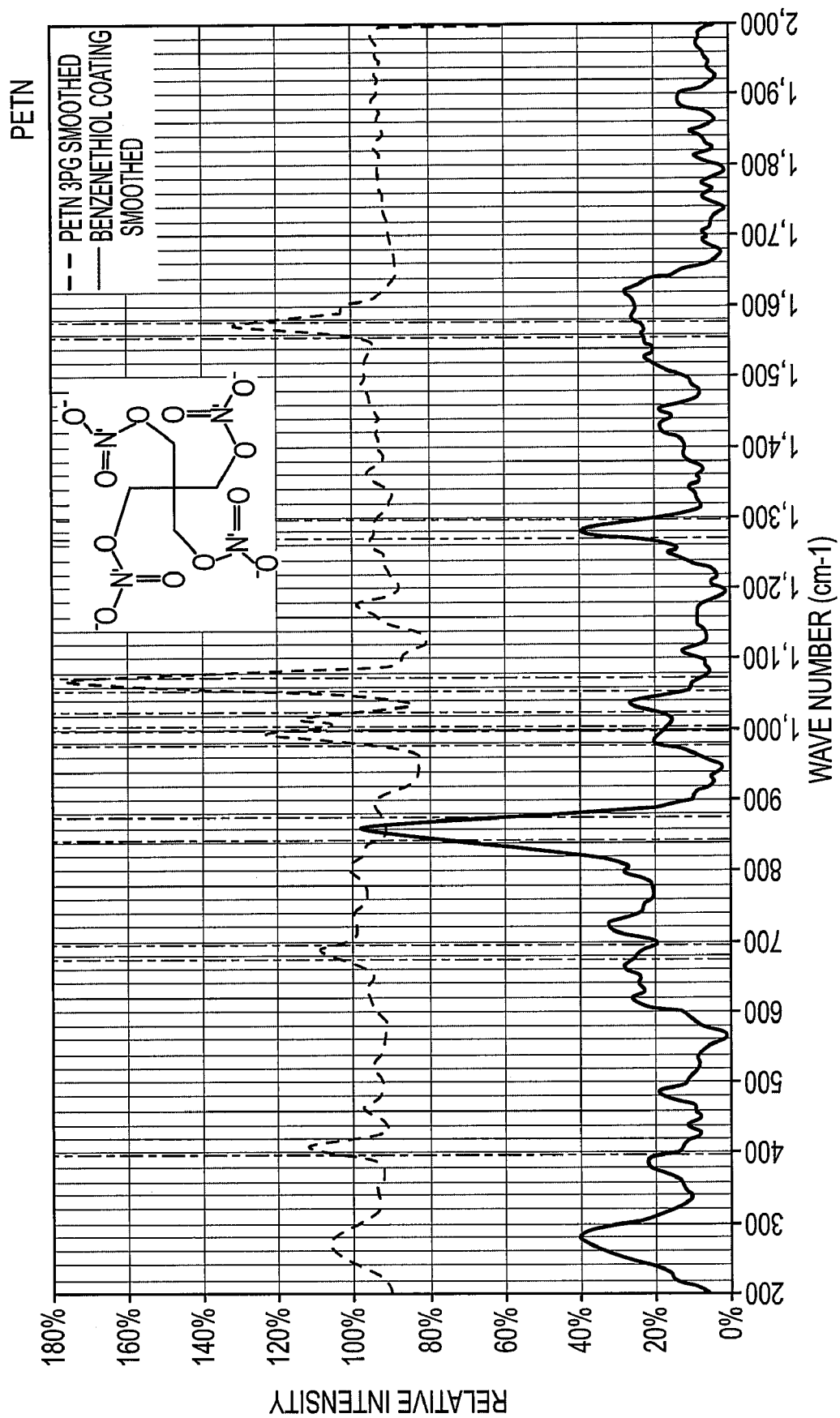
FIG. 31 is a plot of relative intensity (units) (vertical axis) against wave number ($cm^{-1}$).(horizontal axis)
Figure 32:
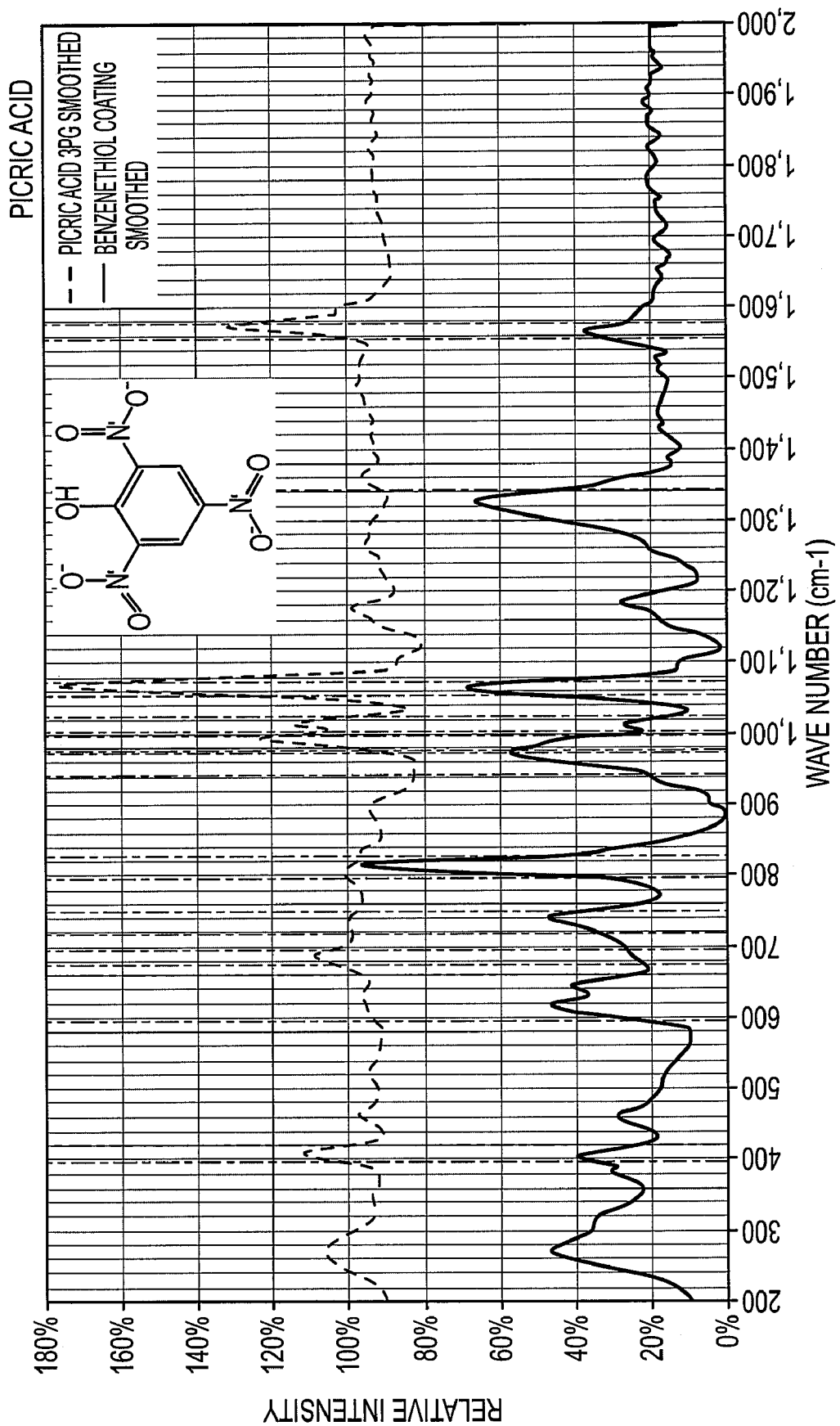
FIG. 32 is a plot of relative intensity (units) (vertical axis) against wave number ($cm^{-1}$).(horizontal axis)
Figure 33:
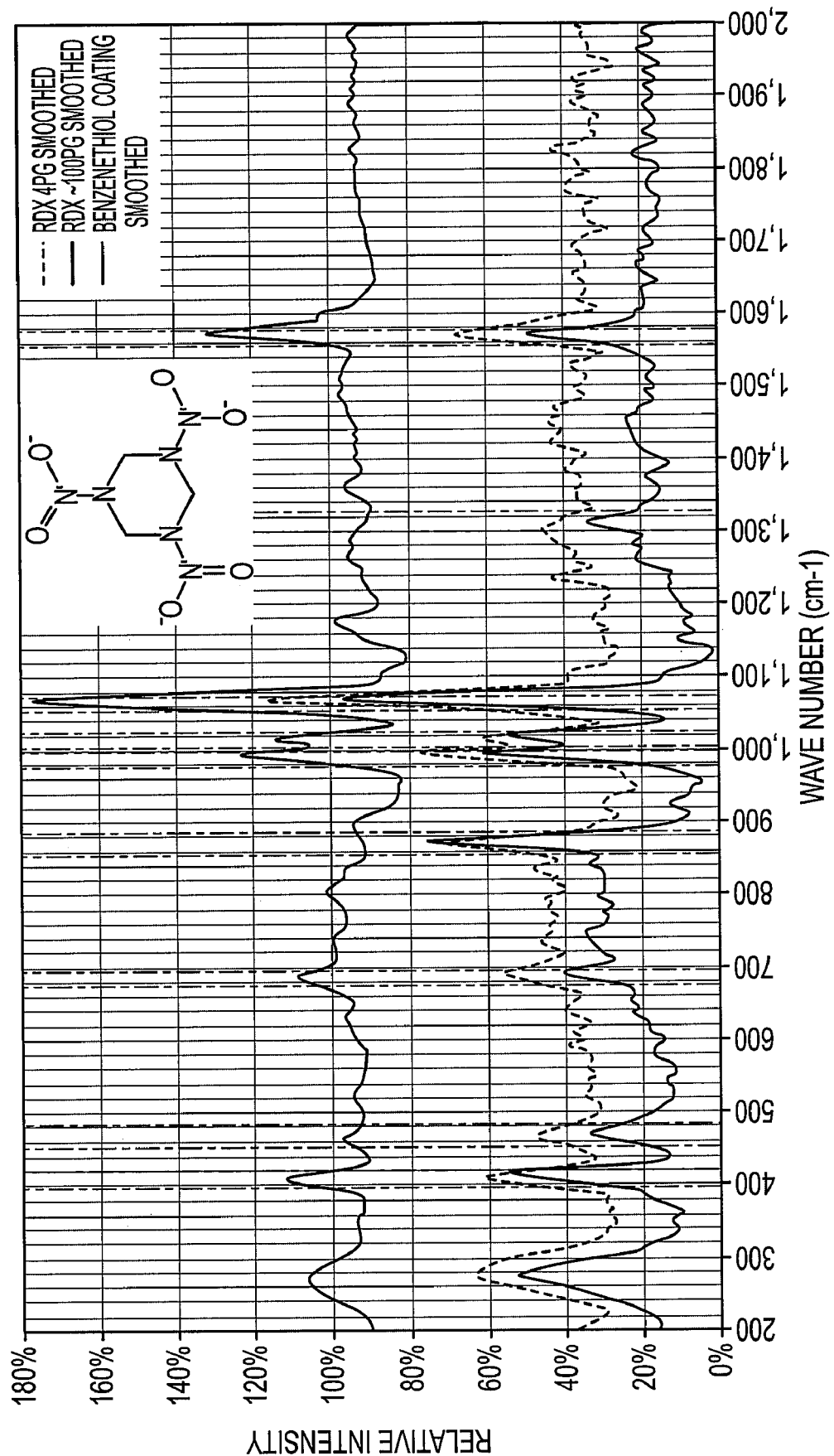
FIG. 33 is a plot of relative intensity (units) (vertical axis) against wave number ($cm^{-1}$).(horizontal axis)
Figure 34:
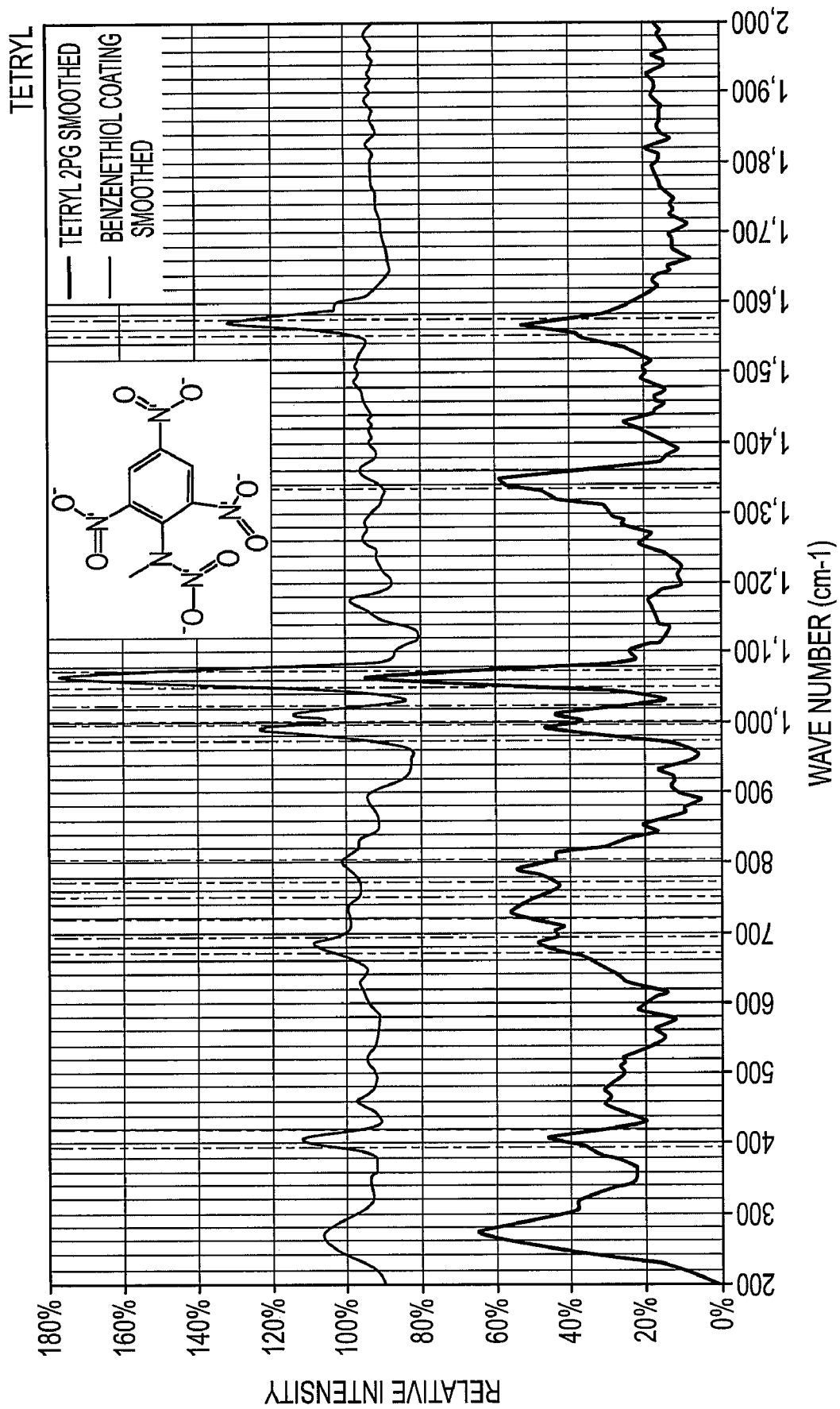
FIG. 34 is a plot of relative intensity (units) (vertical axis) against wave number ($cm^{-1}$).(horizontal axis)
Figure 35:
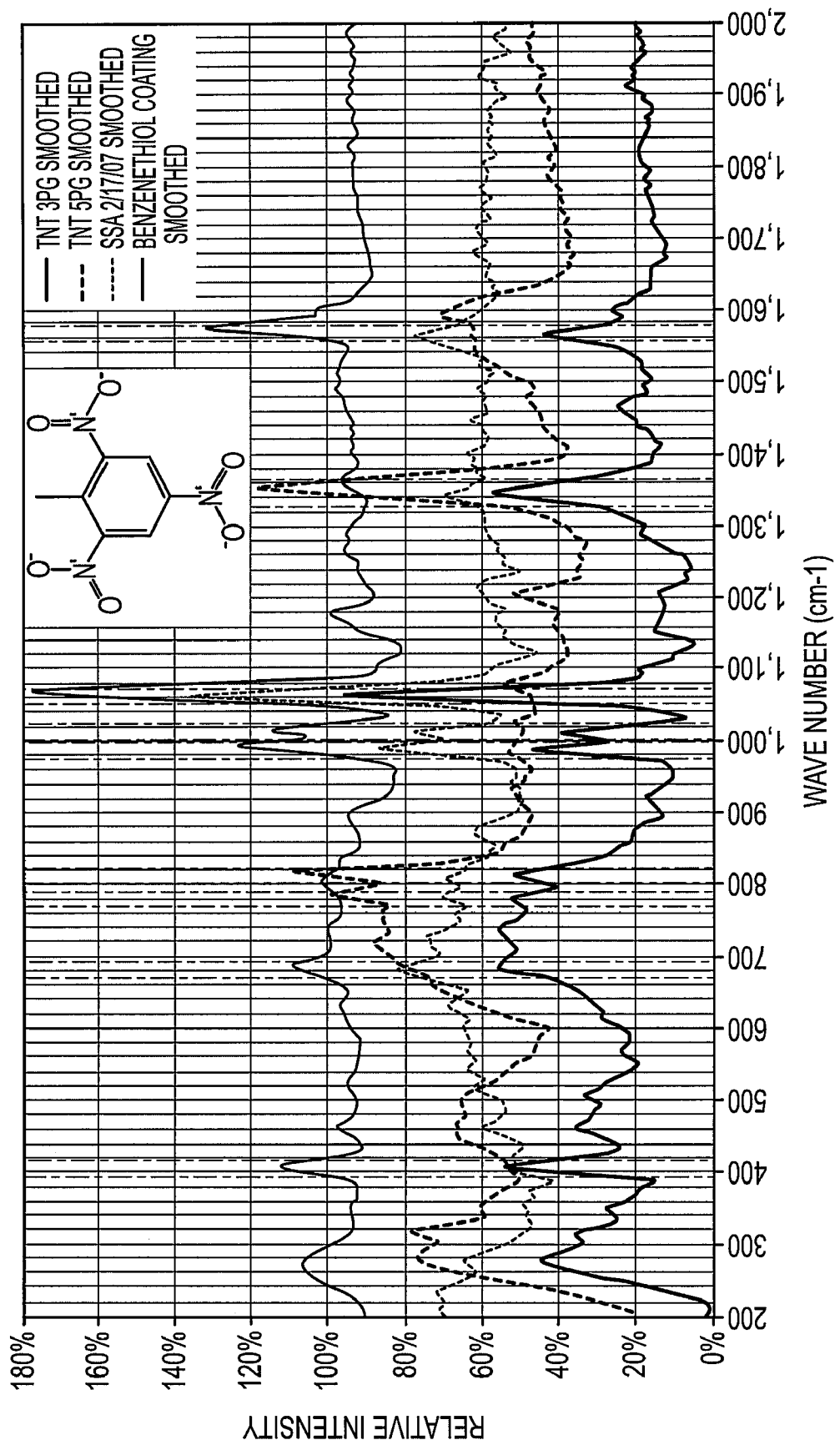
FIG. 35 is a plot of relative intensity (units) (vertical axis) against wave number ($cm^{-1}$).(horizontal axis)

FIGS. 29-35 depict SERS spectra for various trace explosives using uncoated (Klarite) substrates and (SAM) coated (benzenethiol) (Klarite) substrates. The trace explosives tested for are: FIG. 29 (ammonium nitrate), 30 (HMX), 31 (PETN), 32 (picric acid), 33 (RDX), 34 (tetryl), and 35 (TNT). The vertical axes of the plots are relative intensity while the horizontal axes are wave number. Uncoated substrates had an unstable background response (e.g., signal stability measured in a few minutes) in intensity and easily show a Raman response indicative of "burning" of atmospheric and sample constituents adsorbing on the surface. Uncoated substrates were found to be sensitive to a wide range of explosives. The substrates coated with benzenethiol were found to have a background response that was stable to passing atmospheric constituents, and the signal stability was measured over hours instead of minutes. Coated substrates were found to be sensitive to a wide range of explosives.

Finally, FIG. 36 depicts detection results for TNT deposited, in liquid form, on a SERS (Klarite) substrate as compared to TNT deposited, in particulate form, on canvas followed by SSA mobilization of the TNT and adsorption of the entrained TNT with a SERS (Klarite) substrate. The strobe light output 5 Joules of energy in a flash while the Raman was rated at 10 mW/2 s. As can be seen from FIG. 36, the TNT was detected successfully by either technique, with direct liquid TNT deposition providing the strongest spectral response in this example.

A number of variations and modifications of the invention can be used. It would be possible to provide for some features of the invention without providing others.

For example in one alternative embodiment, a detection technique other than SERS is employed. An exemplary alternative detection technique is mass spectrometry, gas chromatography, amplifying fluorescent polymer, and electronic noses.

The present invention, in various embodiments, configurations, or aspects, includes components, methods, processes, systems and/or apparatus substantially as depicted and described herein, including various embodiments, configurations, aspects, subcombinations, and subsets thereof. Those of skill in the art will understand how to make and use the present invention after understanding the present disclosure. The present invention, in various embodiments, configurations, and aspects, includes providing devices and processes in the absence of items not depicted and/or described herein or in various embodiments, configurations, or aspects hereof, including in the absence of such items as may have been used in previous devices or processes, e.g., for improving performance, achieving ease and\or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments, configurations, or aspects for the purpose of streamlining the disclosure. The features of the embodiments, configurations, or aspects of the invention may be combined in alternate embodiments, configurations, or aspects other than those discussed above. This method of disclosure is not to be interpreted as reflecting an intention that the claimed invention requires more features than are expressly recited in each claim. Rather, as the following claims reflect, inventive aspects lie in less than all features of a single foregoing disclosed embodiment, configuration, or aspect. Thus, the following claims are hereby incorporated into this Detailed Description, with each claim standing on its own as a separate preferred embodiment of the invention.

Moreover, though the description of the invention has included description of one or more embodiments, configurations, or aspects and certain variations and modifications, other variations, combinations, and modifications are within the scope of the invention, e.g., as may be within the skill and knowledge of those in the art, after understanding the present disclosure. It is intended to obtain rights which include alternative embodiments, configurations, or aspects to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for detecting a target material, comprising:
providing a metal surface, the metal being at least one member of Group 11 (IB) of the Periodic Table of the Elements;
contacting, in an irradiating chamber, a sample fluid with the metal surface, the sample fluid having a direction of flow, the direction of flow being at a first angle relative to a plane of the metal surface;
irradiating the metal surface with radiation to produce scattered radiation, the radiation having an optical path that is at a second angle relative to the plane of the metal surface, the second angle ranging from about 80 to about 90 degrees;
determining, by a computer, a reference signal, the reference signal being associated with an intensity of radiation scattered by the metal surface in the substantial absence of analytes and/or the reference signal being associated with an intensity of radiation scattered by a coating previously applied to the metal target being adsorbed on the surface;
determining, by a computer, an analyte signal, the analyte signal being associated with an intensity of radiation scattered by analytes located on the metal surface;
determining, by a computer for a selected current measurement, a ratio of the reference signal to an analyte signal; and
analyzing, by a detector, the scattered radiation for spectral information associated with a target material.

2. The method of claim 1, wherein the metal surface is nano-textured and further comprising before the contacting step:
illuminating a surface with a strobe light while applying at least one of a positive and negative fluid pressure to the irradiated surface to form the sample fluid; and
collecting and transporting the sample fluid through a conduit to the irradiating chamber.

3. The method of claim 2, wherein the metal surface is nano-textured, wherein the conduit is unheated and has a length of no more than about 2 cm, and wherein the radiation has a wavelength ranging from about 5330 to about 10640 Angstroms.

4. The method of claim 2, wherein the strobe light and radiation source are located in a handheld unit, wherein the detector and power source are located in a discrete base unit, wherein a fiber optic extends between the handheld unit and the base unit, wherein the handheld unit comprises a head containing the strobe light and radiation source and a handgrip, and wherein the head is rotable relative to the handgrip to adjust a position of the strobe light relative to a surface to be sampled.

5. The method of claim 4, wherein an access door in the head provides access to the metal surface and wherein, when the access door is in an open position, power to the radiation source is switched off and, when the access door in a closed position, power to the radiation source is switched on.

6. The method of claim 1, wherein the irradiating step comprises the substeps:
    passing the radiation through a first lens to form a collimated beam;
    reflecting the radiation off of a beam splitter to direct the collimated beam along the optical path, the beam splitter reflecting at least most of the radiation along the optical path;
    passing the directed collimated beam through a second lens to form a converged beam, the converged beam being focused on the metal surface;
    passing the scattered radiation through the second lens to form a colliminated beam of scattered radiation;
    passing the collimated beam of scattered radiation through the beam splitter, the beam splitter passing at least most of the collimated beam of scattered radiation along a second optical path;
    thereafter passing the collimated beam through a third lens to form a converged beam of scattered radiation, the converged beam of scattered radiation being focused on a fiber optic; and
    transporting, by the fiber optic, the converged beam to the detector.

7. The method of claim 1, wherein the irradiating step comprises the substeps:
    passing the radiation through a beam splitter to direct the beam along the optical path;
    passing the directed radiation through a second lens to form a converged beam, the converged beam being focused on the metal surface;
    passing the scattered radiation through the second lens to form a colliminated beam of scattered radiation;
    reflecting the collimated beam off of the beam splitter, the beam splitter reflecting at least most of the collimated beam along a second optical path;
    thereafter passing the scattered collimated beam through a prism to direct the scattered collimated beam along the second optical path;
    thereafter passing the scattered collimated beam through a second lens to form a converged beam of scattered radiation, the converged beam of scattered radiation being focused on a fiber optic; and
    transporting the converged beam, by the fiber optic, to the detector.

8. The method of claim 1, wherein the first angle is non-zero and has a magnitude of no more than about 65 degrees.

9. The method of claim 1, wherein the first angle ranges from about 65 to about 90 degrees.

10. The method of claim 1, further comprising:
    at least one of heating and cooling, by a thermal-electric device, the metal surface during the contacting step; and
    when the metal surface is cooled and after the contacting step, directing the contacted sample fluid with a heat rejecting side of the thermal-electric device to remove thermal energy.

11. The method of claim 1, further comprising:
    electrically charging, by a first polarity, the sample fluid upstream of the metal surface; and
    wherein the metal surface has a second polarity opposite to the first polarity to electrically attract any target material in the sample fluid.

12. The method of claim 1, wherein the metal surface comprises a plurality of differing regions, each region being configured to adsorb differing target materials, wherein, in the irradiating step, each region is irradiated.

13. A method for detecting a plurality of differing target materials, comprising:
    forming, on a metal surface, a plurality of differing regions, each region being configured to adsorb differing target materials and the metal being at least one member of Group 11 (IB) of the Periodic Table of the Elements;
    contacting, in an irradiating chamber, a sample fluid with the metal surface;
    irradiating, with radiation, each of the plurality of differing regions to produce scattered radiation;
    determining, by a computer, a reference signal, the reference signal being associated with an intensity of radiation scattered by the metal surface in the substantial absence of analytes and/or the reference signal being associated with an intensity of radiation scattered by a coating previously applied to the metal target being adsorbed on the surface;
    determining, by a computer, an analyte signal, the analyte signal being associated with an intensity of radiation scattered by analytes located on the metal surface;
    determining, by a computer for a selected current measurement, a ratio of the reference signal to an analyte signal; and
    analyzing, by a detector, the scattered radiation for spectral information associated with each of the plurality of target materials.

14. The method of claim 13, wherein each of the differing regions has a differing level of affinity for adsorbing differing target materials.

15. The method of claim 14, wherein each of the regions has differing active groups attached to the metal surface.

16. The method of claim 13, wherein, in the contacting step, a direction of flow of the sample fluid is at a first angle relative to a plane of the textured metal surface, wherein, in the thereafter irradiating step, the radiation has an optical path that is at a second angle relative to the plane of the textured metal surface, the second angle ranging from about 80 to about 90 degrees; and further comprising:
    performing, for a selected current measurement, at least one of the following steps:
        (i) determining, by a computer and based on the ratio, a cumulative amount of analyte adsorbed on the metal surface in multiple prior measurements made using the metal surface and the selected current measurement;
        (ii) determining, by a computer and based on the ratio, a remaining operational life of the metal surface, the remaining operational life being related to an amount of active surface remaining in the metal surface; and
        (iii) by a computer, setting a set of zero analyte spectral characteristics equal to spectral characteristics in the analyte signal for the selected measurement, wherein the zero analyte spectral characteristics are later differenced from second spectral characteristics in a second analyte signal to produce delta spectral characteristics, the second analyte signal being from a second measurement performed after the selected measurement, and wherein the delta spectral characteristics is used to detect the presence of additional analytes on the metal surface.

17. A method for processing Raman signals, comprising:
determining, by a computer, a reference signal, the reference signal being associated with an intensity of radiation scattered by a metal surface in the substantial absence of analytes and/or the reference signal being associated with an intensity of radiation scattered by a coating previously applied to the metal target being adsorbed on the surface, the metal being at least one member of Group 11 (IB) of the Periodic Table of the Elements;
thereafter determining, by a computer, an analyte signal, the analyte signal being associated with an intensity of radiation scattered by analytes located on the metal surface;
reusing the metal surface for multiple sample measurements; and
determining, by a computer for a selected current measurement, a ratio of the reference signal to an analyte signal and performing, by a computer, at least one of the following steps:
(i) determining, based on the ratio, a cumulative amount of analyte adsorbed on the metal surface in multiple prior measurements made using the metal surface and the selected current measurement;
(ii) determining, based on the ratio, a remaining operational life of the metal surface, the remaining operational life being related to an amount of active surface remaining in the metal surface; and
(iii) setting a set of zero analyte spectral characteristics equal to spectral characteristics in the analyte signal for the selected measurement, wherein the zero analyte spectral characteristics are later differenced from second spectral characteristics in a second analyte signal to produce delta spectral characteristics, the second analyte signal being from a second measurement performed after the selected measurement, and wherein the delta spectral characteristics is used to detect the presence of additional analytes on the metal surface.

18. The method of claim 17, wherein substep (i) is performed.

19. The method of claim 17, wherein substep (ii) is performed.

20. The method of claim 17, wherein substep (iii) is performed.

21. The method of claim 17, wherein the thereafter determining step comprises the sub-steps:
contacting, in an irradiating chamber, a sample fluid with the metal surface, the sample fluid having a direction of flow, the direction of flow being at a first angle relative to a plane of the textured metal surface;
thereafter irradiating the textured metal surface with radiation to produce scattered radiation, the radiation having an optical path that is at a second angle relative to the plane of the textured metal surface, the second angle ranging from about 80 to about 90 degrees;
analyzing, by a detector, the scattered radiation for spectral information associated with a target material, wherein the metal surface comprises a plurality of differing regions, each region being configured to adsorb differing target materials, wherein, in the irradiating step, each region is irradiated.

* * * * *